(12) United States Patent
Dominik et al.

(10) Patent No.: US 9,839,463 B2
(45) Date of Patent: Dec. 12, 2017

(54) INSTRUMENT FOR USE IN BENDING SURGICAL DEVICES

(71) Applicant: Stryker European Holdings I, LLC, Kalamazoo, MI (US)

(72) Inventors: Robert Dominik, Grandvaux (CH); Jan Heinsohn, Hoboken, NJ (US); Gennaro A. Barile, Secaucus, NJ (US); Andrew Nelson, New City, NY (US); Scott Vormbrock, Kinnelon, NJ (US)

(73) Assignee: Stryker European Holdings I, LLC, Kalamazoo, MI (US)

( * ) Notice: Subject to any disclaimer, the term of this patent is extended or adjusted under 35 U.S.C. 154(b) by 439 days.

(21) Appl. No.: 13/790,459

(22) Filed: Mar. 8, 2013

(65) Prior Publication Data

US 2014/0066994 A1    Mar. 6, 2014

Related U.S. Application Data

(60) Provisional application No. 61/697,439, filed on Sep. 6, 2012.

(51) Int. Cl.
*A61B 17/88* (2006.01)
*B21D 7/06* (2006.01)

(52) U.S. Cl.
CPC .......... *A61B 17/8863* (2013.01); *A61B 17/88* (2013.01); *B21D 7/063* (2013.01)

(58) Field of Classification Search
CPC ... A61B 17/80; A61B 17/808; A61B 17/8085; A61B 17/88; A61B 17/8863; A61B 17/58; B21D 7/063; B21D 7/08
(Continued)

(56) References Cited

U.S. PATENT DOCUMENTS 1,079,442 A * 11/1913 Rutledge ................... 72/390.2
1,402,898 A *  1/1922 Schwerin ............... F16D 41/12
                                                    74/149
(Continued)

FOREIGN PATENT DOCUMENTS

CA        2162837 A1    5/1997
WO    2006047581 A2    5/2006

OTHER PUBLICATIONS

Extended European Search Report for Application No. 13182980.6 dated Mar. 7, 2014.
(Continued)

*Primary Examiner* — Matthew Lawson
*Assistant Examiner* — Amy Sipp
(74) *Attorney, Agent, or Firm* — Lerner, David, Littenberg, Krumholz & Mentlik, LLP

(57) ABSTRACT

A system for bending a surgical device is disclosed in which the system may include a bending apparatus having a housing with a series of posts received therein. In some embodiments, one of the series of posts may be selectively movable within an elongate slot in the housing, while another of the series of posts may be circumferentially movable. Movement of the circumferentially movable post may serve to bend a surgical device about at least one of the other remaining posts. A tool may also be provided with the system for interacting with a lever and causing the circumferentially movable post to move circumferentially. An alternate apparatus for bending a surgical device is also disclosed, as are methods of bending a surgical device using the aforementioned system.

21 Claims, 14 Drawing Sheets

(58) Field of Classification Search
USPC .............................. 606/101; 74/89.18, 575
See application file for complete search history.

(56) References Cited

U.S. PATENT DOCUMENTS

| | | | |
|---|---|---|---|
| 1,628,581 A | | 5/1927 | Dinkel |
| 2,242,135 A | * | 5/1941 | Mertz ........................ 72/174 |
| 2,382,266 A | * | 8/1945 | Simonsen ................. 72/31.05 |
| 2,502,713 A | * | 4/1950 | Fagge .................. B21D 7/022 |
| | | | 72/388 |
| 2,675,723 A | | 4/1954 | Stein |
| 2,678,573 A | | 5/1954 | Taylor |
| 2,737,835 A | * | 3/1956 | Herz ......................... 606/101 |
| 2,986,195 A | * | 5/1961 | Landis ........................ 72/154 |
| 3,464,254 A | * | 9/1969 | Le Breton ................. 72/390.2 |
| 3,620,066 A | | 11/1971 | Henkel |
| 3,822,578 A | * | 7/1974 | Le Breton ................. 72/390.2 |
| 3,842,825 A | | 10/1974 | Wagner |
| 3,875,822 A | * | 4/1975 | Erith .................... B60T 7/102 |
| | | | 254/DIG. 12 |
| 4,223,543 A | * | 9/1980 | Sakamoto ................... 72/30.1 |
| 4,379,400 A | * | 4/1983 | Schwarz ............. B21D 7/063 |
| | | | 72/388 |
| 4,474,046 A | | 10/1984 | Cook |
| 4,587,824 A | | 5/1986 | Wiersema et al. |
| 4,989,441 A | * | 2/1991 | Wagner ..................... 72/390.2 |
| 5,013,314 A | | 5/1991 | Firica et al. |
| 5,113,685 A | | 5/1992 | Asher et al. |
| 5,237,847 A | | 8/1993 | Owens |
| 5,389,099 A | | 2/1995 | Hartmeister et al. |
| 5,490,409 A | | 2/1996 | Weber |
| 5,528,921 A | | 6/1996 | Herman |
| 5,564,302 A | | 10/1996 | Watrous |
| 5,615,572 A | | 4/1997 | Johnson et al. |
| 5,651,283 A | * | 7/1997 | Runciman .................. 72/390.4 |
| 5,653,139 A | * | 8/1997 | Lee ............................. 72/217 |
| D383,841 S | | 9/1997 | Runciman |
| 5,819,571 A | * | 10/1998 | Johnson ............. A61B 17/8863 |
| | | | 72/31.05 |
| 5,819,580 A | | 10/1998 | Gauthier |
| 6,006,581 A | | 12/1999 | Holmes |
| 6,077,271 A | | 6/2000 | Huebner et al. |
| 6,128,944 A | | 10/2000 | Haynes |
| 6,283,969 B1 | | 9/2001 | Grusin et al. |
| 6,374,544 B1 | * | 4/2002 | Ellis ............................ 49/249 |
| 6,497,133 B1 | | 12/2002 | Rose |
| 6,644,087 B1 | | 11/2003 | Ralph et al. |
| 6,931,908 B1 | * | 8/2005 | Mitson ...................... 72/390.2 |
| 7,229,446 B2 | | 6/2007 | Capanni |
| 7,454,939 B2 | | 11/2008 | Garner et al. |
| 7,473,257 B2 | | 1/2009 | Knopfle et al. |
| 7,488,331 B2 | | 2/2009 | Abdelgany |
| 7,740,634 B2 | | 6/2010 | Orbay et al. |
| 7,740,649 B2 | | 6/2010 | Mosca et al. |
| 7,771,433 B2 | | 8/2010 | Orbay et al. |
| 7,909,859 B2 | | 3/2011 | Mosca et al. |
| 7,935,126 B2 | | 5/2011 | Orbay et al. |
| 8,043,298 B2 | | 10/2011 | Capanni |
| 8,141,295 B2 | * | 3/2012 | Carrier ......................... 49/249 |
| 2004/0176780 A1 | * | 9/2004 | Knopfle et al. ............. 606/105 |
| 2005/0192577 A1 | * | 9/2005 | Mosca et al. ................. 606/69 |
| 2006/0150698 A1 | | 7/2006 | Garner et al. |
| 2007/0074559 A1 | * | 4/2007 | Boulin ....................... 72/389.9 |
| 2008/0269805 A1 | * | 10/2008 | Dekutoski et al. .......... 606/279 |
| 2009/0222020 A1 | | 9/2009 | Schmuck et al. |
| 2009/0254326 A1 | * | 10/2009 | Isaacs ............................ 703/11 |
| 2009/0318979 A1 | | 12/2009 | Raines et al. |
| 2010/0268119 A1 | * | 10/2010 | Morrison .................... 600/587 |
| 2011/0062204 A1 | * | 3/2011 | Aebi .................. A61B 17/8863 |
| | | | 225/102 |
| 2011/0092981 A1 | | 4/2011 | Ng et al. |
| 2011/0178522 A1 | | 7/2011 | Orbay et al. |
| 2011/0264100 A1 | | 10/2011 | Sixto, Jr. et al. |
| 2011/0270262 A1 | | 11/2011 | Justis et al. |
| 2012/0247173 A1 | * | 10/2012 | Paris ................. A61B 17/8863 |
| | | | 72/362 |

OTHER PUBLICATIONS

Partial European Search Report for Application No. EP13182980 dated Dec. 9, 2013.

* cited by examiner

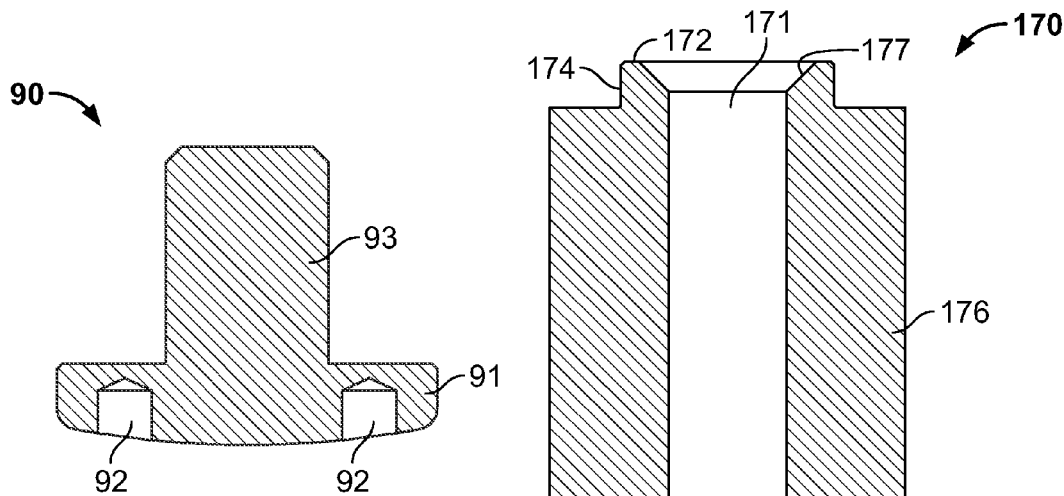
FIG. 3G
FIG. 3H
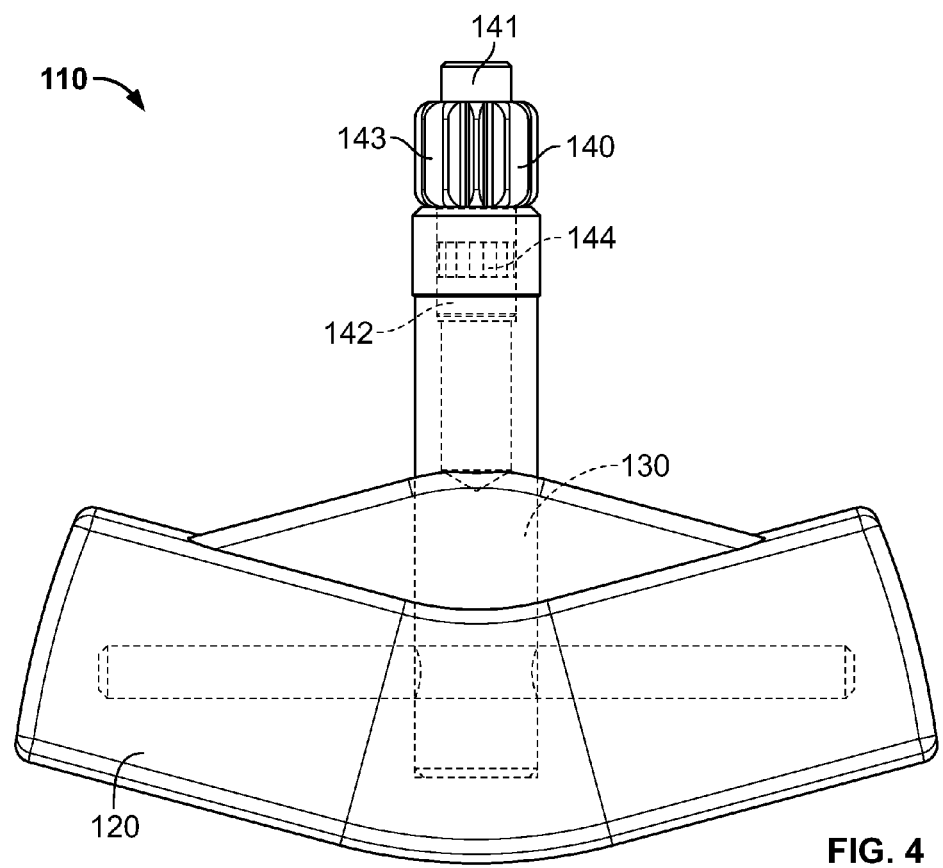
FIG. 4

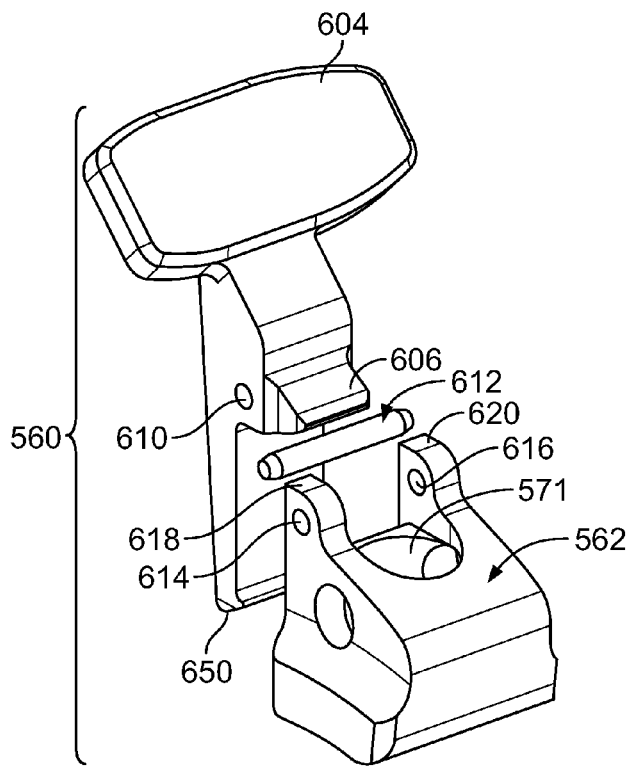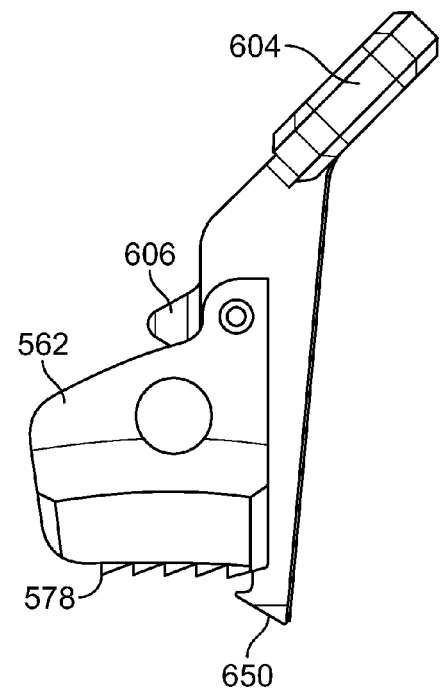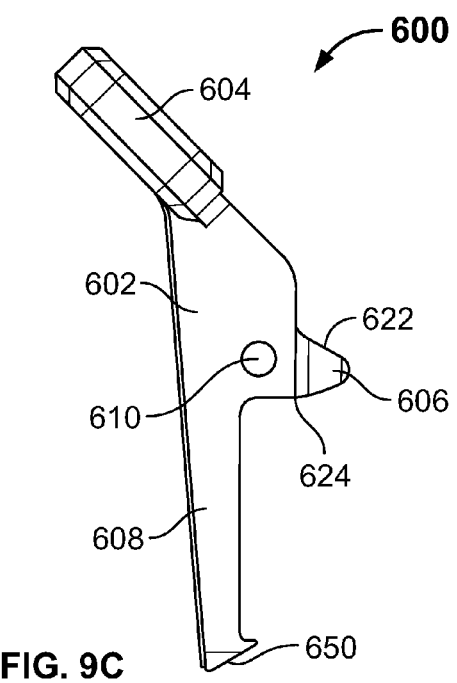
FIG. 9A
FIG. 9B
FIG. 9C

INSTRUMENT FOR USE IN BENDING SURGICAL DEVICES

CROSS-REFERENCE TO RELATED APPLICATIONS

The present application claims the benefit of the filing date of U.S. Provisional Patent Application No. 61/697,439, filed Sep. 6, 2012, the disclosure of which is hereby incorporated by reference herein.

BACKGROUND OF THE INVENTION

The present invention relates, in general, to devices for use in bending metal or other materials, and specifically, to tools for bending bone plates or other surgical devices.

Various types of surgical devices (e.g., bone plates, surgical rods, or other implantable devices) are commonly used to, inter alia, treat or reduce fractures of bone, correct deformities and/or alignment of bones, including in the spine, and fuse or otherwise treat damaged bones, most notably, vertebral bodies. Particular applications of such surgical devices may require the surgical device to conform to the shape of the bone being treated, which may be necessary, for example, in regions of the body such as near the clavicle, in spinal applications, or in other areas. Certain surgical devices may be pre-contoured for this purpose (i.e., to conform to a particular bone shape), and may therefore satisfy the particular demands of a patient. However, in many cases patients have varying anatomical confines, which make it difficult to pre-contour a particular surgical device to meet the needs of all patients. Given this limitation, the surgical device, when lacking the proper contour, must be shaped or bent to match the surface of bone to which it is being applied.

Numerous tools have been developed to assist with proper contouring of various surgical devices. Many of these tools are hand tools generally configured as pliers-type devices with handles for gaining leverage and applying a bending force to the plate or other device being contoured. Examples of such bending pliers are found in U.S. Pat. Nos. 7,473,257, and 7,229,446, among others. Table top bending apparatus are also used, as shown, for example, in U.S. Pat. No. 6,644,087. In many cases, however, it may be difficult to gain the necessary leverage to bend the bone plate or other device, which may place strain on the surgeon or other user of the tool. The particular bending apparatus used may also be too large and/or cumbersome to utilize effectively during a surgical procedure. Further, precision bending is a significant issue when using the aforementioned bending devices.

Therefore, there exists a need for an improved bending apparatus, which is easier to utilize.

BRIEF SUMMARY OF THE INVENTION

A first aspect of the present invention provides a system for bending a surgical device, the system comprising a bending apparatus including a housing with at least a first and a second post, the first and second posts being fixable in location during bending. A third circumferentially movable post may also be engaged with the housing, and a first actuator may be provided to interact with the third post to move the post circumferentially, such that the surgical device is bent about at least one of the first and second posts.

In some embodiments of the first aspect, the third post is configured to move circumferentially upon rotation of the first actuator about an axis thereof. In other embodiments, the first actuator comprises a shaft having a longitudinal axis, and the shaft is configured to cause circumferential movement of the third post upon rotation of the shaft about the axis.

A second aspect of the present invention includes a method of bending a surgical device comprising the step of providing a bending apparatus having a housing with at least first, second, and third posts, the third post being circumferentially movable. The method also includes the steps of: (1) providing a first actuator that is movable between a first position and a second position to move the third post circumferentially, a portion of the first actuator being engageable with a structure attached to the third post; and (2) rotating the portion of the first actuator with respect to the structure to move the third post circumferentially and bend the surgical device about at least one of the first and second posts.

Certain embodiments of the second aspect also include the steps of moving at least one of the first and second posts within an elongate slot in the housing, or stabilizing the first actuator with respect to the housing by inserting a shaft of the actuator through an aperture in a first plate of the housing and into a corresponding aperture in a second plate of the housing. The first actuator, in some cases, may also include a first gear mechanism engageable with a second gear mechanism situated adjacent the housing. Rotation of the first gear mechanism with respect to the second gear mechanism may also cause circumferential movement of the third post.

A third aspect of the invention provides a bending apparatus for bending a surgical device. The bending apparatus may include a housing having first, second, and third posts, at least the third post being circumferentially movable about the housing, and an actuator movable between a first position and a second position to move the third post circumferentially, a portion of the actuator being engageable with a structure attached to the third post. At least one of the first, second, and third posts may also be movable within an elongate slot in the housing.

In some cases, the actuator may include an end with a first gear mechanism. The bending apparatus may also include a second gear mechanism adapted to engage with the first gear mechanism, the second gear mechanism being movable upon movement of the actuator between the first position and the second position, wherein the first post is engaged with a portion of the second gear mechanism.

BRIEF DESCRIPTION OF THE DRAWINGS

A more complete appreciation of the subject matter of the present invention and of the various advantages thereof can be realized by reference to the following detailed description in which reference is made to the accompanying drawings in which:

FIGS. 3A-H are various top and cross-sectional views of several of the components of the instrument of FIG. 1.

FIG. 4 is a partial transparent view of the wrench of FIG. 1.

FIGS. 9A-E are various perspective and cross-sectional views of yet another releasable locking mechanism according to an embodiment of the present invention.

DETAILED DESCRIPTION

In describing particular embodiments of the present invention, specific terminology will be used for the sake of clarity. However, the invention is not intended to be limited to any specific terms used herein, and it is to be understood that each specific term includes all technical equivalents, which operate in a similar manner to accomplish a similar purpose.

Figure 1:
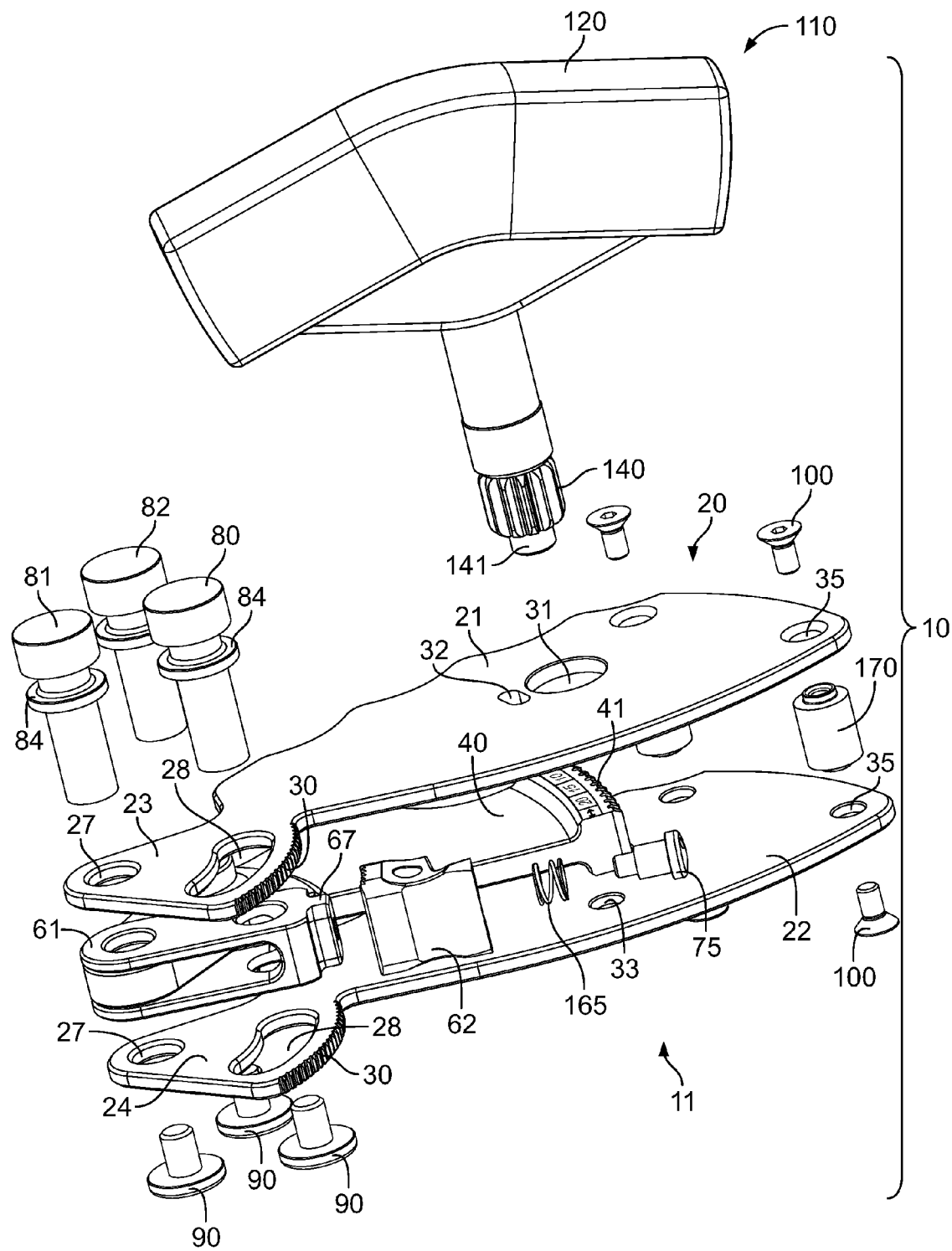
FIG. 1 is an exploded perspective view of the components of an instrument for bending surgical devices, according to one embodiment of the present invention.
Figure 6A:
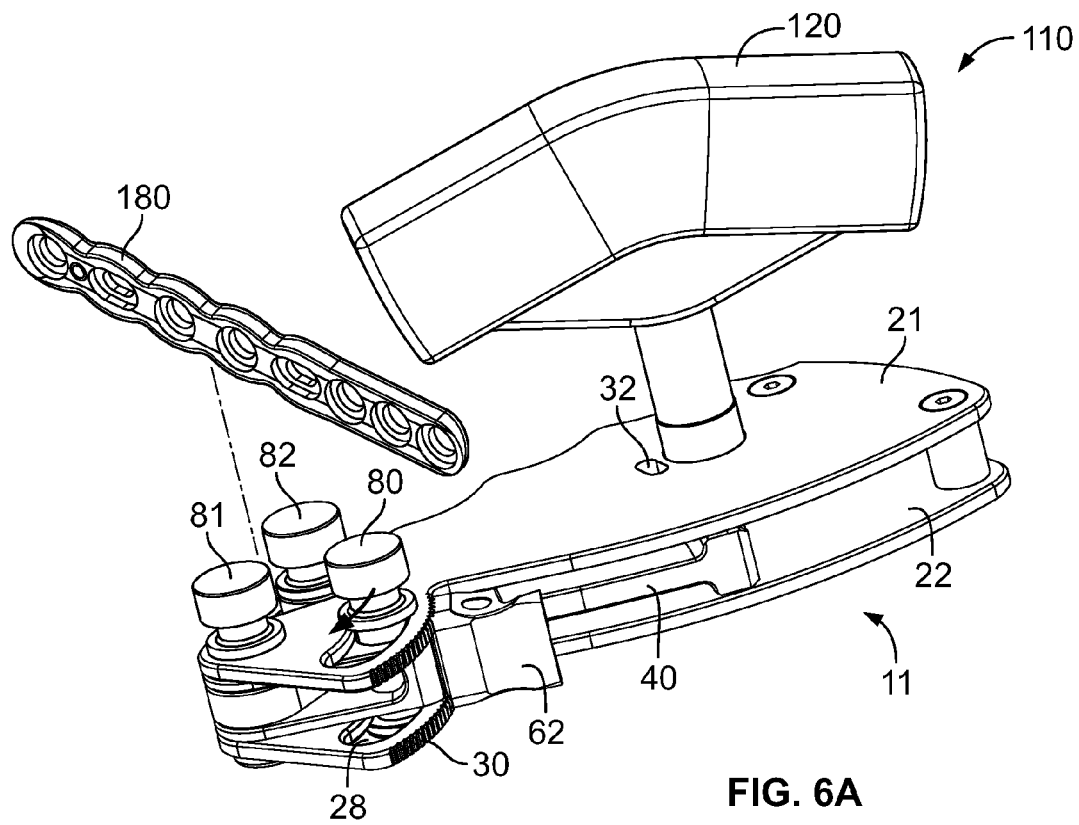
FIGS. 6A-B are perspective views of the instrument of FIG. 1 in use.
Figure 6B:
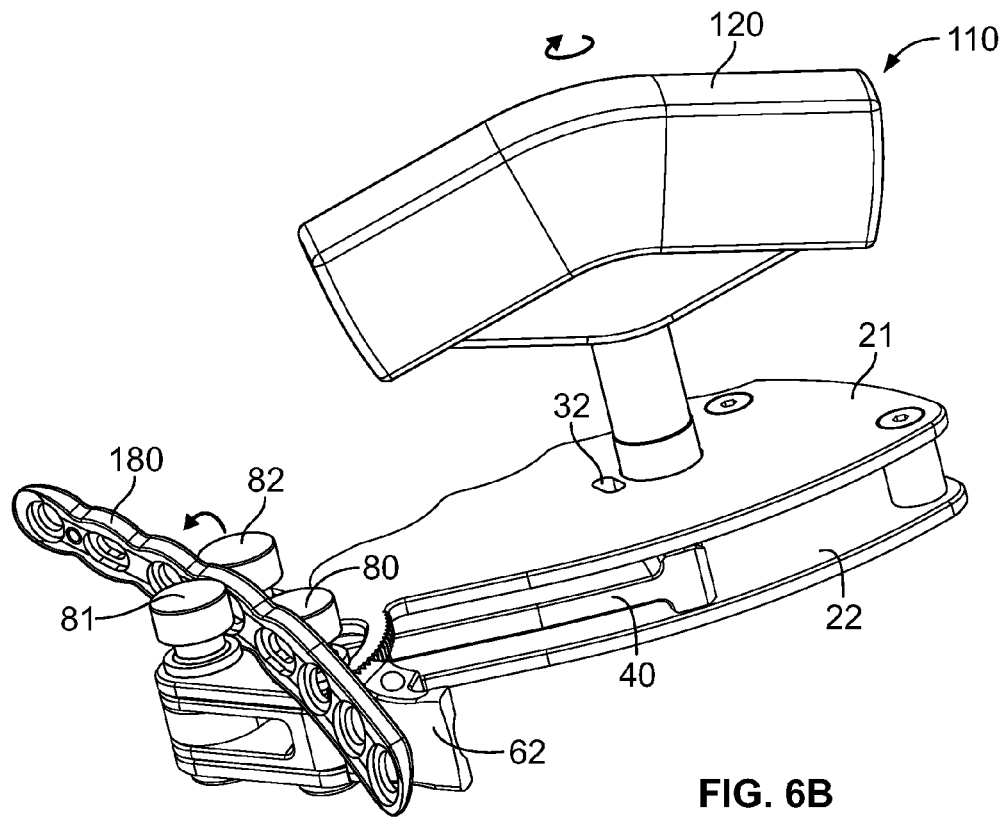

Referring to FIG. 1, there is shown a tool 10 for use in bending bone plates, rods, or other surgical devices (hereinafter, simply a "surgical device" or the "surgical devices") including, generally: (1) a bender 11 having a housing 20; (2) a series of posts 80, 81, 82 for situating the surgical device within; (3) a lever 40 having a rack 41 and apertures 45, 46 (best shown in FIG. 3A) for connecting with posts 81, 82; and (4) a wrench 110 having a pinion 140 for interacting with rack 41. In use, the surgical device may be situated among posts 80, 81, 82, and the lever 40 may be actuated via rack 41 and pinion 140 causing post 82 attached to lever 40 to move circumferentially and bend the surgical device about at least post 81, as is best illustrated in FIGS. 6A and 6B. This construction, as described in more detail below, provides a surgeon, nurse, or other skilled practitioner (hereinafter "the user") with increased leverage and precision in bending a variety of surgical devices.

Figure 2A:
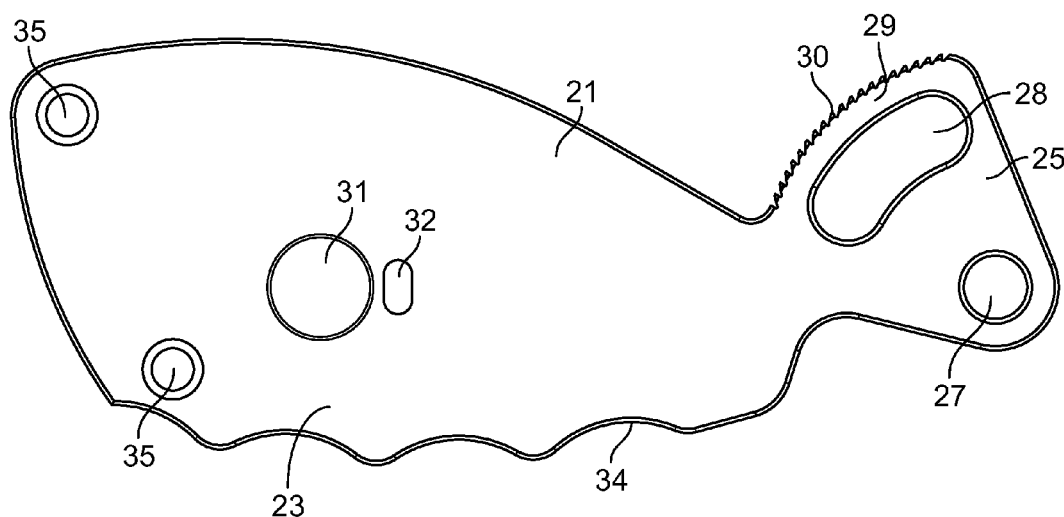
FIGS. 2A-B are top and bottom views of the first and second plates of the housing shown in FIG. 1.
Figure 2B:
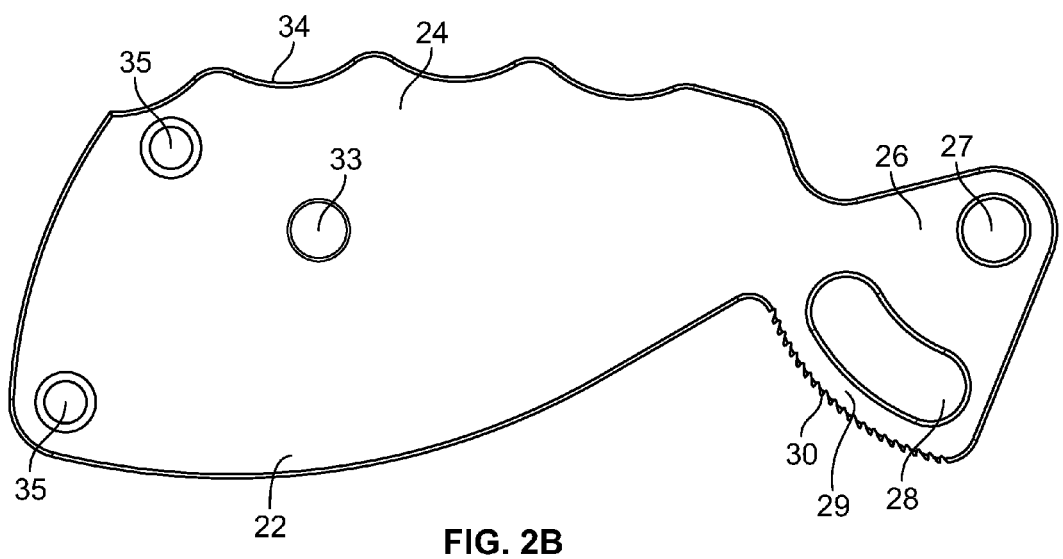

Referring to FIGS. 1 and 2A-2B, housing 20 may comprise a first plate 21 (FIG. 2A) and a second plate 22 (FIG. 2B) situated in an opposed relationship with respect to one another, the plates 21, 22 being connected upon assembly. First and second plates 21, 22 may each include a handle portion 23, 24 and a foot portion 25, 26. Foot portions 25, 26 may have an aperture 27 for receiving a post 81 and an elongate slot 28 for receiving a separate post 80, the latter of which may, in one embodiment, have a curvature corresponding to a rounded portion 29 adjacent the slot 28. A series of teeth 30 may also be formed on rounded portion 29.

Handle portion 23 of first plate 21 may further contain an aperture 31 sized to allow a pinion 140 on wrench 110 therethrough, and a separate aperture 32 for viewing angular indicia 42 formed on a portion of lever 40. Further, as shown in FIGS. 1 and 2B, second plate 22 may include an aperture 33 opposed to aperture 31 on first plate 21 for receiving an end portion 141 of pinion 140, and thus stabilizing wrench 110 during use. Each of plates 21, 22 may also have a series of opposed and corresponding apertures 35 for receiving respective pegs 100. In some embodiments, handle portion 23, 24 of plates 21, 22 may include finger-gripping sections 34 for accommodating a user's hand during operation.

Figure 3A:
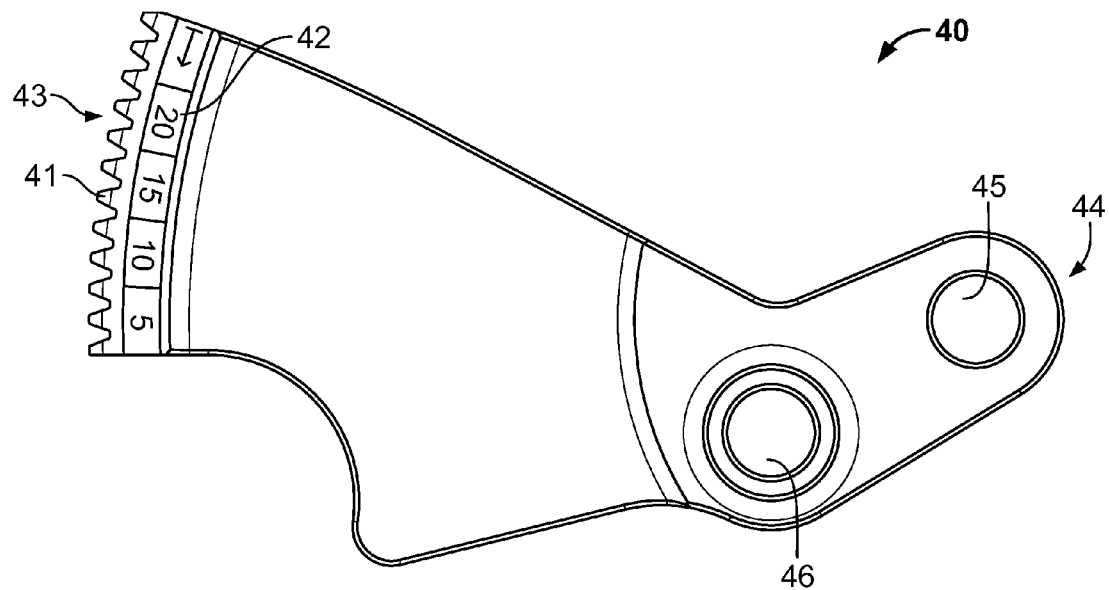
Figure 3B:
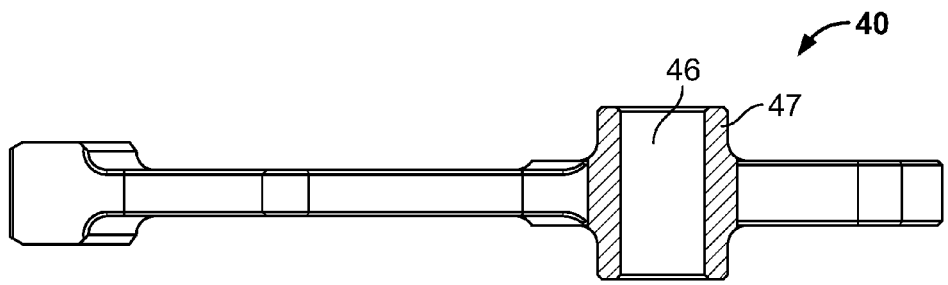

Further components of the tool 10 of FIG. 1 are shown in detail in FIGS. 3A-H. In particular, FIG. 3A depicts a lever 40 having, at one end 43, a rack 41 and angular indicia 42; and, at an opposing end 44, a set of apertures 45, 46. Aperture 45 is generally configured to receive post 81, while aperture 46 is configured to receive post 82. In some embodiments, end 43 may be angled with respect to opposing end 44, and the area surrounding aperture 46 may be raised so as to form a bore or tube 47, as shown in detail in the cross-section of lever 40 depicted in FIG. 3B.

Figure 3C:
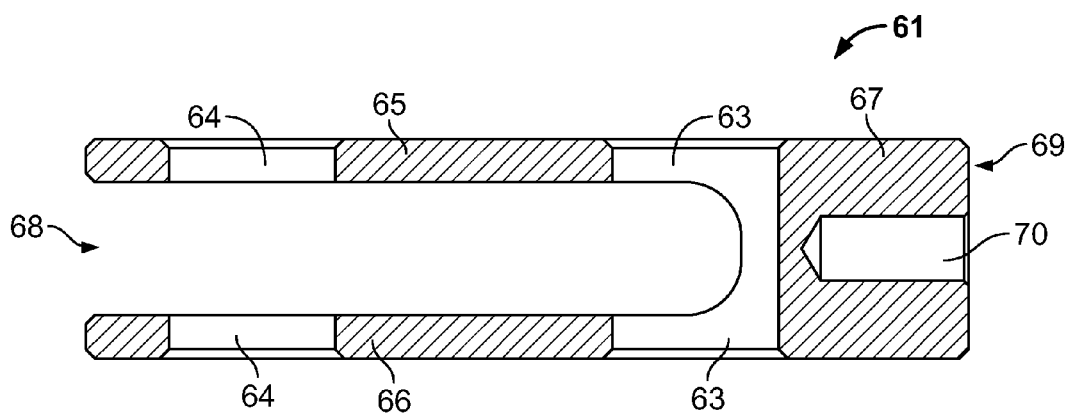
Figure 3D:
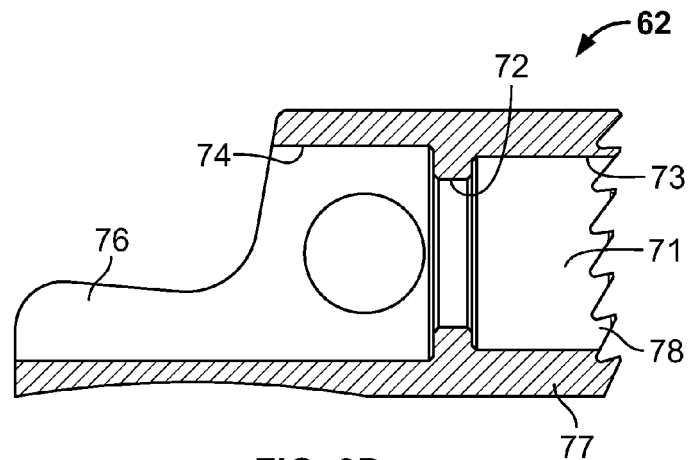
Figure 3E:
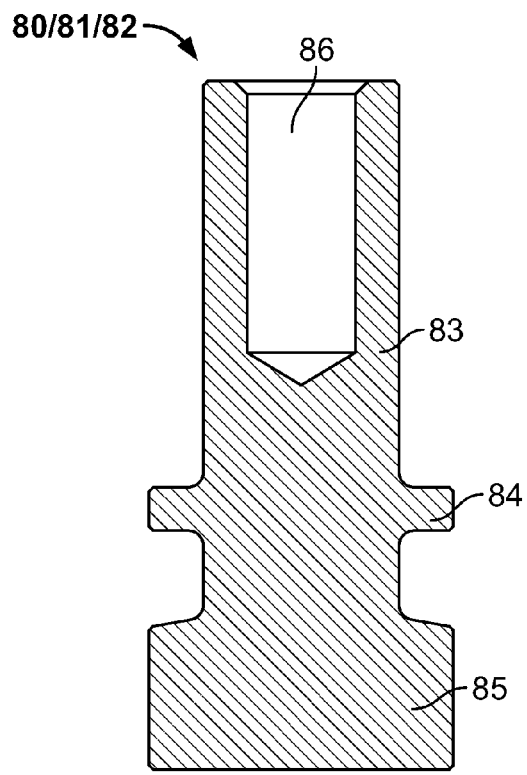

FIGS. 3C-3D depict portions of an adjustment mechanism, as shown in exploded view in FIG. 1, including a rotatable or pivotal bar 61 (FIG. 3C) and a fixing member 62 (FIG. 3D). Bar 61, as illustrated in FIG. 3C, may include a set of arms 65, 66 spaced apart from one another and, in some embodiments, arranged generally parallel to one another. Arms 65, 66 may also be open at one end 68 so as to interact with end 44 of lever 40, as described more fully below. Further, apertures 63, 64 may be formed within each of arms 65, 66 for generally interacting, respectively, with one of posts 80, 81 (i.e., aperture 63 with post 80 and aperture 64 with post 81). A protrusion 67 may also be situated on an opposing and closed end 69 of bar 61 for interacting with a portion of fixing member 62. In some embodiments, a bore 70 may be formed in a surface of protrusion 67.

Fixing member 62, as shown in FIG. 3D, may include a bore 71 therethrough with a step 72 formed midway through the bore 71. A first section 73 of bore 71 at one side of step 72 may be configured to interact with protrusion 67 on pivotal bar 61, and a second section 74 of bore 71 at the other side of step 72 may be designed to interact with a pin 75, shown best in FIGS. 1 and 3F. Fixing member 62 may also have a finger-gripping section 76 and a relatively thicker end section 77 having teeth 78 for engaging with teeth 30 on first and second plates 21, 22.

FIGS. 3E-H, respectively, illustrate cross-sectional views of: (1) posts 80, 81, 82; (2) pin 75; (3) caps 90; and (4) hubs 170, as also shown in FIG. 1. Posts 80, 81, 82 may each generally include a shaft 83, a flange 84 disposed on shaft 83, and a head portion 85. An interior of posts 80, 81, 82 also may contain a bore 86.

Pin 75 may have a head portion 160 with a set of key slots 161 for accepting a tool (not shown) therein. Adjacent head portion 160 may also be a shaft 162 having two sections 163, 164 of decreasing diameter.

Caps 90, similar to pin 75, may include a head portion 91 with key slots 92 and a shaft 93. Shaft 93 of caps 90, however, may be of relatively constant diameter in one embodiment.

Hubs 170, as shown in FIG. 3H, may be generally cylindrical in shape with a longitudinal bore 171 running therethrough. Ends 172, 173 of hubs 170 may be generally identical and may each include an extension 174, 175 of reduced diameter with respect to a body 176 of the hub 170. Further, in some embodiments, extensions 174, 175 may have a tapered region 177, 178 within bore 171 for receiving a portion of one of pegs 100, as shown in FIG. 1. Extensions 174, 175 may also be configured for insertion within one of apertures 35 in first or second plate 21, 22.

Figure 5:
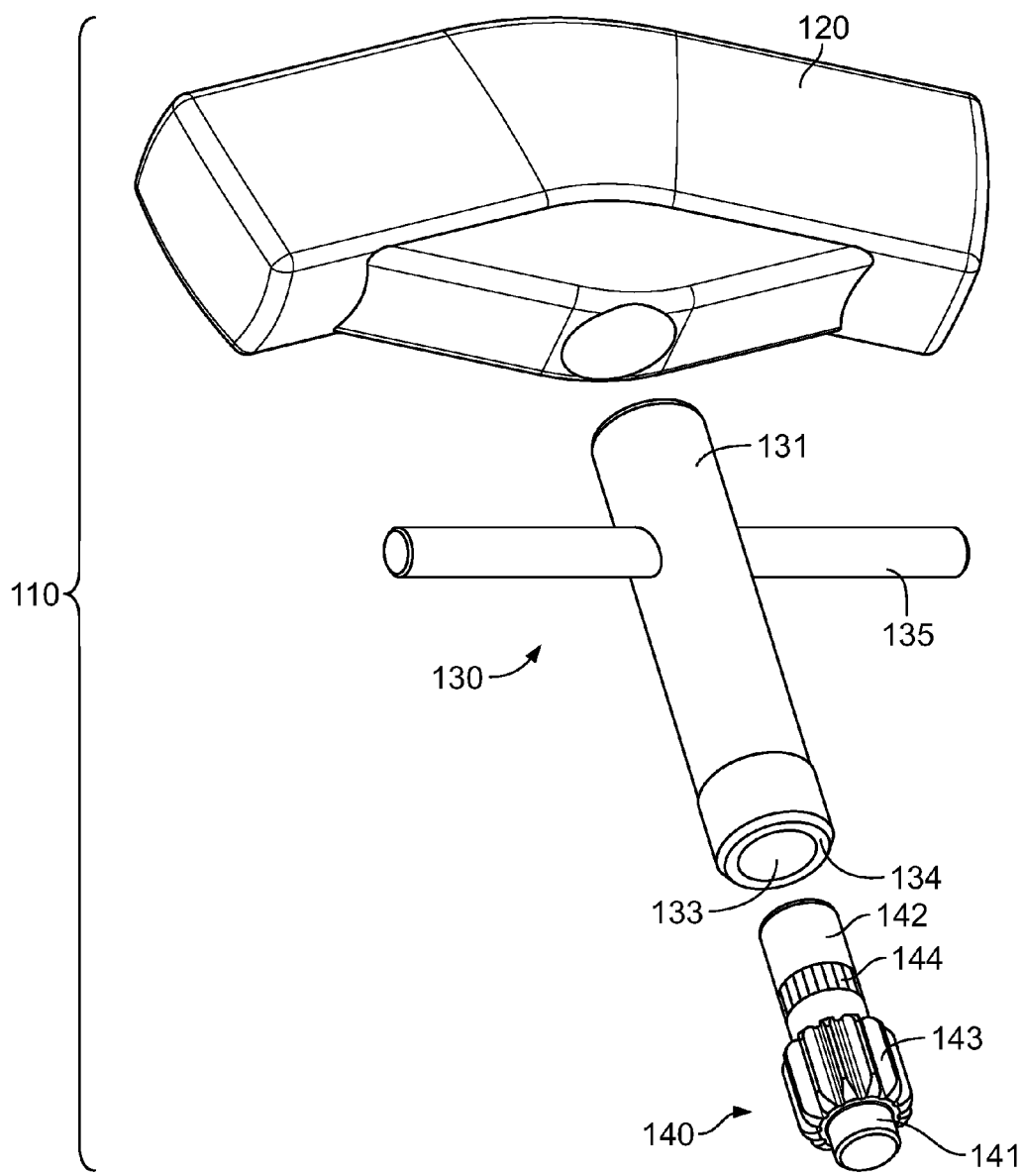
FIG. 5 is an exploded view of the wrench of FIG. 4.

Referring now to FIGS. 4-5, a wrench 110 may be provided with the aforementioned system for actuating lever 40 and bending the surgical device. Wrench 110 may contain a handle 120, within which a T-member 130 may be inserted (shown in dotted lines in FIG. 4), and a pinion 140 extending from the T-member 130. T-member 130, as shown in FIG. 5, may comprise a first rod 131 having a transverse bore (not shown) formed therethrough, and a longitudinal bore 133 at an end 134 of the rod 131. To complete T-member 140, a second rod 135 may be inserted within the transverse bore in rod 131. This finished construct may then be situated within handle 120. In some embodiments T-member 130 may be positioned within a recess (not shown) in handle 120 after manufacture, or, alternatively, handle 120 may be molded over T-member 130 upon construction.

Wrench 110 also may include a pinion 140 having a shaft 142 with a generally toothed first section 143 and a notched or serrated second section 144 that may be inserted within longitudinal bore 133 of T-member 130. In particular, the notched second section 144 of pinion 140 may be inserted within longitudinal bore 133, while the toothed first section 143 may be left to reside out of bore 133, as shown in FIG. 4. A third section or end 141 of shaft 142 may extend from and adjacent to the first toothed section 143, with the third section or end 141 having a smaller diameter than first section 143. Upon assembly of wrench 110, as shown in FIG. 4, such device may operate in conjunction with bender 11 in the manner described below.

Prior to using bender 11 and wrench 110 to bend a surgical device, the components of such devices may be assembled as follows. Referring to FIG. 1, first and second plates 21, 22 of housing 20 may be connected through opposed and corresponding apertures 35 via pegs 100, and apertures 27 and elongate slots 28 via posts 81, 80 and corresponding caps 90. In particular, referring to both FIGS. 1 and 3H, extensions 174, 175 of hubs 170 may be situated within apertures 35 in first and second plates 21, 22, and then pegs 100 may be inserted through apertures 35 and into bores 171 of cylindrical hubs 170. Pegs 100 and corresponding bores 171 may optionally be threaded for this purpose.

Likewise, referring now to FIGS. 1 and 3A-C, with arms 65, 66 of pivotal bar 61 situated about aperture 45 of lever 40, and such components disposed between plates 21, 22, post 81 may be inserted through aperture 27 in first plate 21, into and through apertures 64, 45 in pivotal bar 61 and lever 40, respectively, and through aperture 27 in second plate 22 to receive corresponding cap 90. Cap 90 may be inserted into bore 86 in post 81, which is shown in detail in FIG. 3E. Further, post 80 may be inserted through elongate slot 28 in first plate 21, into and through aperture 63 in pivotal bar 61, and through elongate slot 28 in second plate 22 to receive corresponding cap 90. As before, cap 90 may be inserted into bore 86 in post 80. Subsequently (or at any point during the process), post 82 may be inserted through aperture 46 in lever 40 and joined with corresponding cap 90, which is inserted within bore 86 of post 82. Flanges 84 of posts 80, 81 may also reside adjacent to or contact a portion of plate 21 to prevent over insertion of posts 80, 81 into elongate slot 28 or aperture 27, respectively. Notably, post 82 may not be inserted through any portion of plates 21, 22, allowing such post to move freely (e.g., in a circumferential direction) upon actuation of lever 40. Further, post 82 may act as a stop surface during use by contacting plates 21, 22 and limiting circumferential movement of lever 40 therein (e.g., in one direction).

With the aforementioned components assembled, fixing member 62 (FIG. 3D), and specifically the first section 73 of the bore 71 thereof, may be inserted over protrusion 67 on pivotal bar 61 and secured thereto via pin 75, as shown in FIG. 1. In a particular embodiment, pin 75 (FIG. 3F) may be inserted into second section 74 of bore 71 until such a point as head 160 abuts or is situated adjacent step 72 of fixing member 62, and section 164 of shaft 162 is situated within bore 70 in protrusion 67. Section 163 of shaft 162 of pin 75 may also be arranged adjacent to a portion of protrusion 67. As seen in FIG. 1, a spring 165 may be associated with pin 75 and may be arranged between pin 75 and bore 71 of fixing member 62, such that, upon insertion of section 164 of pin 75 in bore 70 of protrusion 67, compression may result between pin 75 and spring 165, thus keeping fixing member 62 (or rather teeth 78) engaged with teeth 30 on plates 21, 22. This may be achieved via rotation of pin 75 through key slots 161, which in one embodiment may thread section 164 into bore 70 of protrusion 67. In particular, spring 165 may be situated to reside on step 72 of fixing member 62, and shaft 162 of pin 75 may be inserted through spring 165, such that head 160 of pin is situated adjacent step 72 and in contact with spring 165. With second section 164 of shaft 162 of pin 75 engaged to pivotal bar 61, spring 165 may therefore allow the user to actuate fixing member 62 (e.g., by pulling such member 62), so that teeth 78 are disengaged from teeth 30 on first and second plates 21, 22. Upon release of fixing member 62, teeth 78 may then re-engage with teeth 30 on plates 21, 22 (e.g., via spring 165) to secure fixing member 62 in place.

When teeth 78 of fixing member 62 are engaged with teeth 30 on first and second plates 21, 22, as described above and shown in exploded view in FIG. 1, corresponding post 80 may be fixed within elongate slot 28. Conversely, upon disengaging teeth 78 of fixing member 62 with teeth 30 on first and second plates 21, 22, post 80 may slide within the track formed by elongate slot 28, and thus may be moved to a number of different positions. Upon reaching a desired position, a user may simply reengage teeth 78 of fixing member 62 with teeth 30 of first and second plates 21, 22 (e.g., via pin 75 and spring 165, as set forth above) to fix post 80 within elongate slot 28. This may allow a user to change the point at which the surgical device may be bent, and also may affect the force which may be applied during the bending process. Further, moving post 80 within elongate slot 28 as described above may also allow the user to more easily remove the surgical device after bending. In other words, after the surgical device is bent via bender 11, post 80 may be moved within elongate slot 28 to provide more space between posts 80, 81, 82 and the bent surgical device. The bent device may therefore be removed more easily after use of bender 11.

Upon assembling the components of tool 10, including the bender 11 and wrench 110 in the manner described above or otherwise, a user may bend a surgical device 180, such as that shown in FIG. 6A-6B. To achieve this, a user may first insert the surgical device 180, which in this case is depicted in FIG. 6A as a bone plate, within and across posts 80, 81, 82 of bender 11. During such insertion, the user may elect to move post 80 within elongate slot 28 to more easily accommodate surgical device 180, and then the user may move post 80 in the direction of the arrow in FIG. 6A to tighten posts 80, 81, 82 about surgical device, if desired.

With the surgical device 180 disposed across posts 80, 81, 82 in the manner shown, the user may then couple wrench 110 with bender 11. In particular, the user may grasp wrench 110 via handle 120 and insert pinion 140, and the end portion 141 thereof, through aperture 31 in first plate 21, and into corresponding aperture 33 in second plate 22. With end portion 141 of pinion 140 disposed in aperture 33 in second plate 22, wrench 110 may be stabilized with respect to bender 11, and pinion 140 may be engaged with rack 41 on lever 40. A user may then rotate handle 120 of wrench 110 causing pinion 140 to rotate within rack 41, and thereby force post 82 circumferentially outward in conjunction with lever 40 (e.g., in the direction of the arrow adjacent post 82 in FIG. 6B). All the while, the user may view angular indicia 42 on lever through aperture 32 in first plate 21 to determine the degree to which surgical device 180 is bent.

As an example, if upon inserting surgical device 180 within and across posts 80, 81, 82 angular indicia 42 reads fifteen (15) degrees, the user may rotate lever 40 via wrench 110 in the manner described above so that the angular indicia 42 shown reads twenty (20) degrees. From this, the user may know that the surgical device 180 being bent has been contoured by about five (5) degrees. Accordingly, the difference between the initial angle read and the final angle may determine the amount by which surgical device 180 is bent.

In using wrench 110, a user may have the option of rotating wrench 110 a continuous three hundred and sixty (360) degrees while coupled with bender 11, and while leaving pinion 140 engaged with rack 41. Alternatively, it is contemplated that wrench 110 may contain structure (not shown) allowing wrench 110 to act as a ratchet-wrench. Thus, a user may alternatively rotate handle 120 of wrench 110 a particular amount, resulting in bending of surgical device 180, and then the user may utilize ratcheting structure (not shown) to re-rotate handle 120 back to its initial position and repeat the procedure. This may provide a user with ease and convenience in bending surgical device 180.

By utilizing the aforementioned rack 41 and pinion 140 mechanism of tool 10, the user may be provided with increased leverage by a factor of fifteen (15) or more. Stated differently, upon rotating wrench 110 while pinion 140 is engaged with rack 41, the amount of force applied by a user may be multiplied by a factor of fifteen (15) or more. It is therefore easier for the user to bend surgical device 180, and such bending may be accomplished with even greater precision due to angular indicia 42 on lever 40. Further, to change the point at which surgical device 180 is bent, or otherwise affect the forces applied to surgical device 180 during the bending process, the user may uncouple the teeth 78 on fixing member 62 from the teeth 30 on rounded portion 29 of first and second plates 21, 22 to allow post 80 to move within elongate slot 28 (e.g., in the direction indicated by the arrow adjacent post 80 in FIG. 6A, or in an opposing direction). Post 80 may then be moved within the track formed by elongate slot 28 to a position in which bending of surgical device 180 may be altered (e.g., the forces or angles at which surgical device 180 may be bent are changed). Teeth 78 on fixing member 62 may then be reengaged with teeth 30 on first and second plates 21, 22, optionally via the actuation of fixing member 62, and post 80 may be re-fixed in place. The user may then utilize wrench 110 in the manner described above to cause bending of surgical device 180 about at least post 81, with such bending being altered due to movement of post 80.

The user may also alter the location of post 80 within elongate slot 28 (e.g., according to the arrow in FIG. 6A, or in an opposing direction) to accommodate surgical devices 180 of varying shapes and/or sizes. For example, various bone plates may be pre-countered to match a particular bone surface or for specific applications in the body, and the user may situate post 80 within elongate slot 28 to accommodate those bone plates of differing sizes and/or contours. An even further use for movement of post 80 within slot 28 may be to allow the user to more easily remove any of the aforementioned surgical devices 180 from without posts 80, 81, 82. As an example, after bending of surgical device 180 in the manner described above, a user may simply move post 80 within slot 28 to create additional space between posts 80, 81, 82 and allow easy removal of surgical device 180 from posts 80, 81, 82. Thus, multiple uses and benefits are contemplated in allowing post 80 to move within elongate slot 28 in plates 21, 22.

Upon bending surgical device 180 as described above and shown in the progression between FIGS. 6A-6B, the user may then remove device 180 from posts 80, 81, 82 and apply it to bone at the surgical site. The surgical device 180 may therefore be contoured specifically to the needs of a patient, and with greater precision and ease.

Figure 7A:
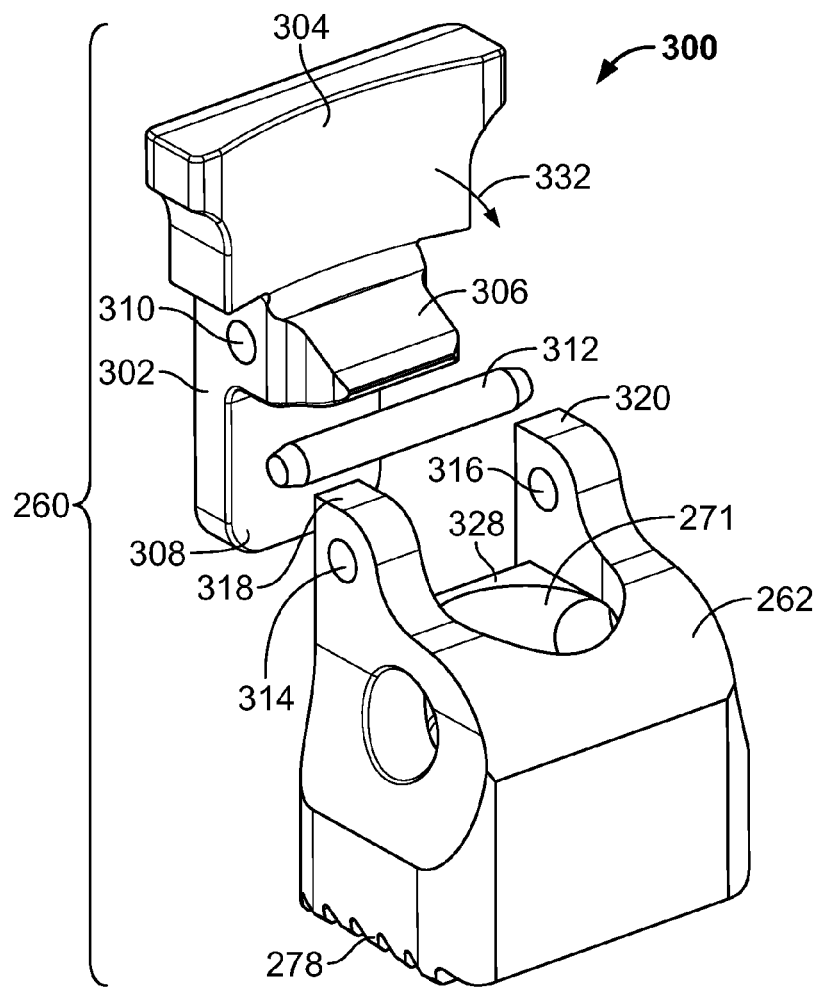
FIG. 7A-D are perspective and cross-sectional views of a releasable locking mechanism used with an alternate embodiment instrument according to the present invention, with FIG. 7D showing the locking mechanism in use.

An alternate version adjustment mechanism 260 is shown in perspective in FIG. 7A and includes a fixing member 262 similar to fixing member 62 described above. Here, like numerals refer to like elements and only the structures differing from tool 10 will be described. Adjustment mechanism 260 may, therefore, be substituted for fixing member 62 used with tool 10, and tool 10 may function in the manner described, except for that set forth below.

As shown in detail in FIGS. 7A-D, adjustment mechanism 260 may include a fixing member 262 having a bore 271 with a first 273 and second section 274 divided by a step 272. As with above, step 272 may serve to engage with spring 165 and pin 75 in the manner discussed. In short, spring 165 may be situated on step 272 and pin 75 may be inserted through spring 165, such that head 160 is engaged with spring 165 and section 164 of shaft 162 of pin 75 is engaged with bore 70 of protrusion 67. As such, spring 165 and pin 75 may function in substantially the same manner as set forth above in relation to fixing member 62, and thus, may serve to compress teeth 278 against teeth 30 of plates 21, 22. Likewise, spring 165 and pin 75 may allow teeth 278 of fixing member 262 to disengage from teeth 30, although this is achieved via an actuator 300, as set forth in detail below.

As with fixing member 62, first section 273 of bore 271 of fixing member 262 may also be configured to interact with protrusion 67 on pivotal bar 61. A set of bores 314, 316 may also be formed through respective receiving members 318, 320 extending from fixing member 262 (e.g., for receiving pin 312).

Figure 7B:
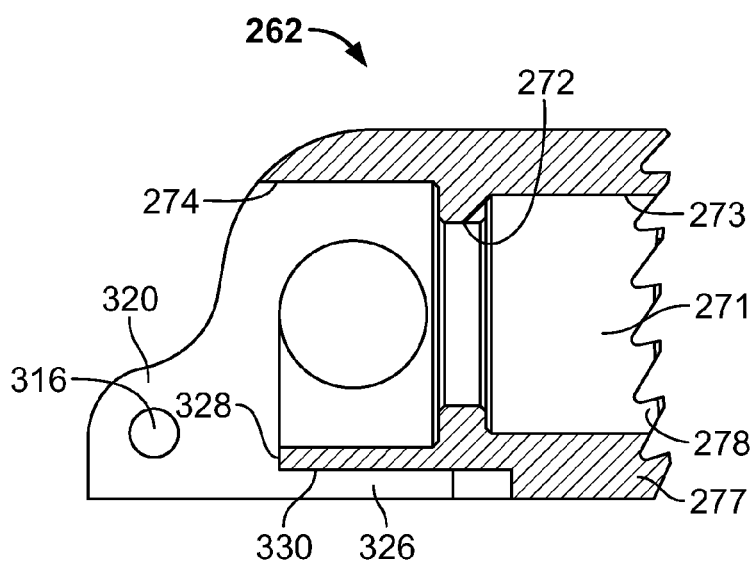
Figure 7C:
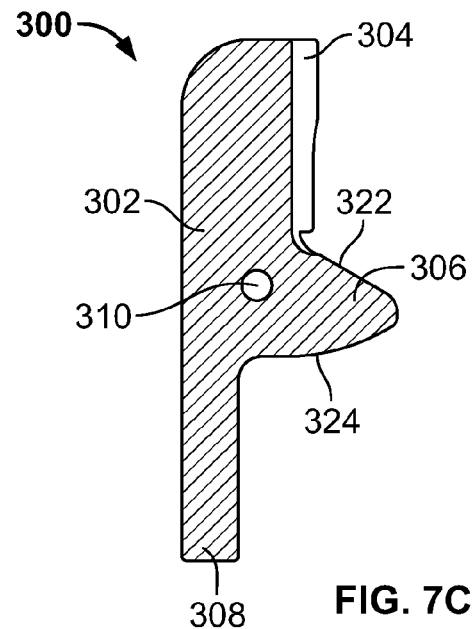

Referring to FIGS. 7A and 7C, adjustment mechanism 260 may also include an actuator 300. Actuator 300, in one embodiment, may have a body 302 with a top finger-contacting portion 304, a flange 306 extending from body 302, and a lower projecting section 308 extending from flange 306. Body 302 of actuator 300 may also include a bore 310 therethrough for receiving a pin 312, which may connect actuator 300 with fixing member 262, as set forth below.

As depicted in detail in FIG. 7C, flange 306 of actuator 300 may have a top surface 322 and a bottom surface 324 offset with respect to the top surface 322. Stated differently, bottom surface 324 may extend deeper into body 302 of actuator 300 relative to top surface 304. Further, both top surface 322 and bottom surface 324 may converge or taper towards one another, in one embodiment.

In use, actuator 300 may be coupled with fixing member 262 via the insertion of pin 312 through bore 314 in receiving member 318, into and through bore 310 in body 302 of actuator 300, and through bore 316 in receiving member 320 of fixing member 262. In this configuration, projecting section 308 of actuator 300 may lie within a recess 326 formed in fixing member 262 (FIG. 7B), and bottom surface 324 of flange 306 may engage with a ledge 328 surrounding bore 271 of fixing member 262. Alternatively, or in addition, bottom surface 324 of flange 306 may engage with a top surface of head 160 of pin (i.e., once inserted into bore 271). Once assembled in this manner, actuator 300 may be biased to remain in an orientation in which projecting section 308 lies flush with a wall 330 adjacent recess 326 of fixing member 262 (FIG. 7B). In other words, actuator 300 may be depressed such that projecting section 308 moves away from wall 330, as shown in detail by the dotted lines in FIG. 7D; however, once released, projecting section 308 may revert back to its initial position against wall 330, as shown by the solid lines in FIG. 7D. In one embodiment, the interaction between bottom surface 324 of flange 306 and pin 75 (e.g., inserted through spring 165) may cause this biasing action.

Figure 3F:
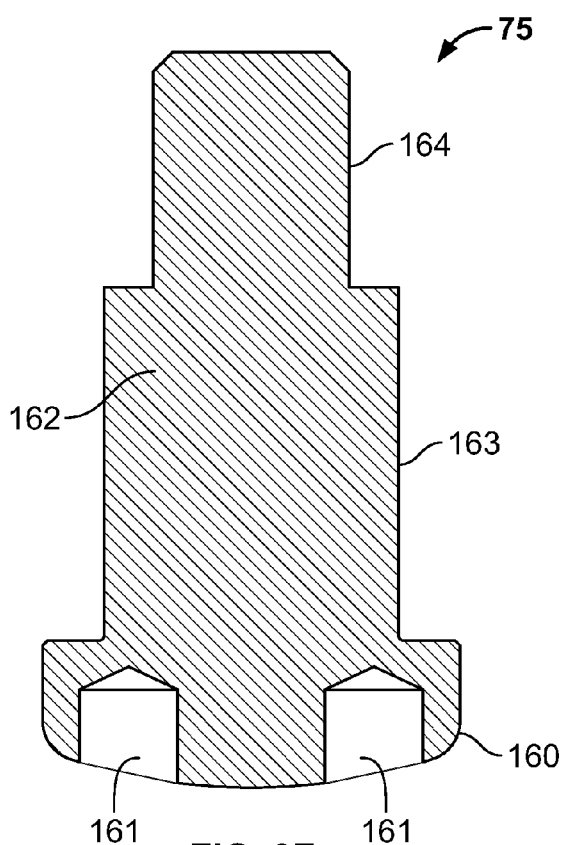

Once constructed, adjustment mechanism 260 may be substituted for the adjustment mechanism described and depicted in FIGS. 1, 3D, and 3F and utilized with bender 11. In particular, adjustment mechanism 260 may be oriented with respect to bender 11 as follows (FIG. 7D)—teeth 278 of fixing member 262 may be engaged with corresponding teeth 30 on plates 21, 22, and flange 306 of actuator may face generally inwards. With adjustment mechanism 260 arranged as such, spring 165 inserted into bore 271 of fixing member 262 may serve to keep teeth 278 on fixing member 262 and teeth 30 on plates 21, 22 engaged (e.g., through interaction with head 160 of pin 75). Teeth 278 and teeth 30 may also be adapted to engage one another, such that movement of fixing member 262 in one direction is easier than in an opposing direction. Specifically, in one embodiment, movement of fixing member 262 generally in the direction of arrow 340 in FIG. 7D may be more difficult than in an opposing direction, since, predominantly, the forces borne on post 80 during bending may be in the direction of arrow 340 (i.e., due to forces exerted on post 80 by the surgical device being bent). Stated differently, since during bending of a surgical device 180 post 80 may tend to be forced in the direction of arrow 340, teeth 278 on fixing member 262 and teeth 30 on plates 21, 22 may be adapted to resist movement of post 80 in that direction. But, in an opposing direction, teeth 278 and teeth 30 may be arranged such that post 80 may move more easily in the opposing direction. This may be accomplished by angling teeth 278 and teeth 30 generally away from arrow 340, as shown in FIGS. 1 and 7D.

To manipulate and/or move post 80 prior to or during the course of bending a surgical device (e.g., surgical device 180), one may utilize actuator 300. In particular, finger-contacting portion 304 of actuator 300 may be adapted to be engaged by a user's finger, such that the user may depress or rotate portion 304 about pin 312. To be exact, the user may depress finger-contacting portion 304 about pin 312, causing portion 304 to move according to the dotted lines in FIG. 7D. This action may cause bottom surface 324 of flange 306 of actuator 300 to contact ledge 328 of fixing member 262 and/or pin 75 engaged with spring 165, and thereby disengage, at least partially, teeth 278 of fixing member 262 from teeth on plates 21, 22. Stated differently, upon depressing finger-contacting portion 304 as shown in FIG. 7D, bottom surface 324 of flange 306 may contact ledge 328 of fixing member 262 and/or pin 75 and spring 165, which, due to the downward force of flange 306 on ledge 328 and/or pin 75, may cause a corresponding upward force on fixing member 262. In this way, fixing member 262 may be "lifted," such that teeth 278 on fixing member 262, at least partially, disengage with teeth 30 on plates 21, 22 to allow movement of fixing member 262 (and thus post 80) generally along slot 28.

Figure 7D:
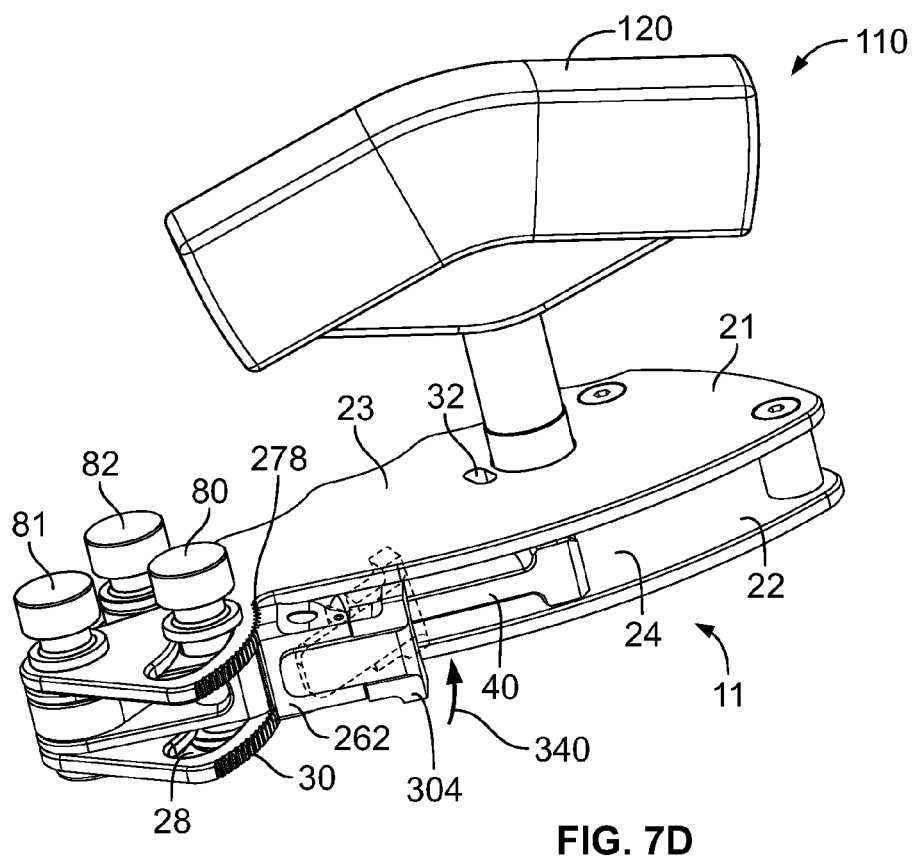

As an example, alternate adjustment mechanism 260 may allow a user to easily contact finger-gripping portion 304 with his/her thumb, while grasping handle portions 23, 24 with his/her other fingers, and depress such portion 304 by flexing the thumb, which causes portion 304 to move to the position shown in dotted lines in FIG. 7D. Through this action (e.g., through flexion of a user's thumb against finger-gripping portion 304), a user may move post 80 in a direction indicated by arrow 340. Further, as noted above, such direction, in one embodiment, may be the direction in which it is more difficult to move post 80. Thus, actuator 300 may assist with allowing a user to disengage teeth 278 on fixing member 262 from teeth 30 on plates 21, 22 to move post 80 in the direction of arrow 340. What is more, to move post 80 in an opposing direction (e.g., the "easier" direction), the user may simply push on finger-contacting portion 304 to cause post 80 to move within slot 28 in an opposing direction to arrow 340. Since teeth 278 and teeth 30 are angled to allow movement in this direction, the user may not need to depress actuator 300 to disengage the aforementioned teeth 278, 30 from one another. Rather, teeth 278 on fixing member 262 and teeth 30 on plates 21, 22 may simply slide past one another. After release of the user's thumb from finger-contacting portion 304 of actuator 300, teeth 278 on fixing member 262 may re-engage with teeth 30 on plates 21, 22 (e.g., through the compression resulting between pin 75 and spring 165), since fixing member 262 is biased to remain in this orientation.

As such, a user may utilize adjustment mechanism 260 in the manner described above to move post 80 within slot 28 in plates 21, 22, either in the direction of arrow 340, or in an opposing direction. Such movement may allow a surgical device 180 to be easily removed from without posts 80, 81, 82 and/or alter the bending characteristics of bender 11, as previously described. Adjustment mechanism 260 further allows one-handed operation, as set forth above.

Figure 9D:
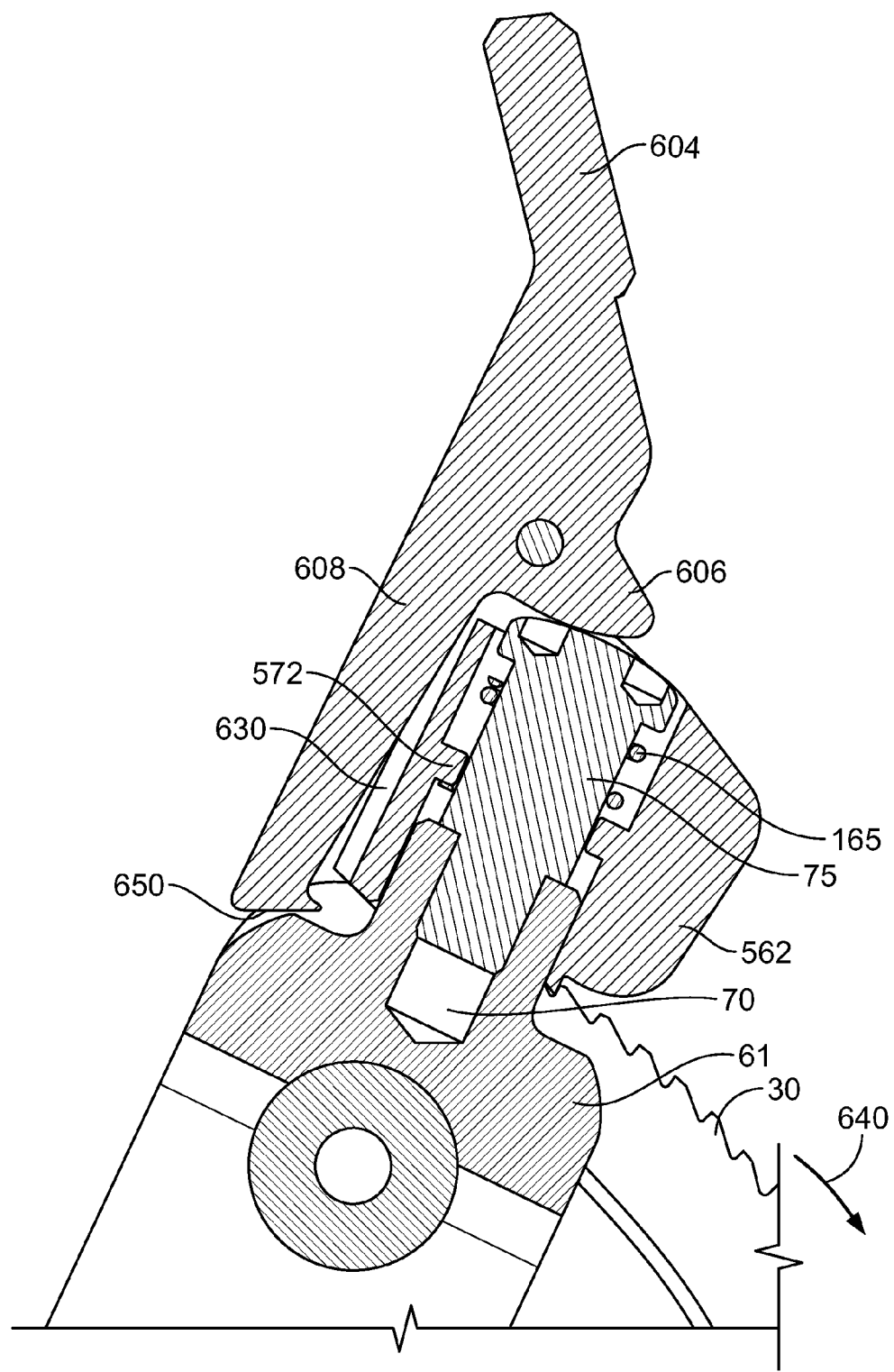

Yet another adjustment mechanism 560 is shown in perspective in FIG. 9A and includes a fixing member 562 similar to fixing members 62, 262 described previously. Here, like numerals refer to like elements and only the structures differing from previous embodiments will be described. Adjustment mechanism 560 may, therefore, be used with tool 10 in the manner described in previous sections with respect to the other adjustment mechanisms, except for that set forth below.

Like adjustment mechanism 260, adjustment mechanism 560 may include: (1) a fixing member 562 having virtually the same construction as fixing member 262 (e.g., teeth 578, a bore 571 with a step 572, and receiving members 618, 620 with apertures 614, 616 for receiving a pin 612); and (2) a pin 612 for connecting an actuator 600 of adjustment mechanism 560 to fixing member 562. But, actuator 600 may be constructed slightly differently than actuator 300 to provide different functionality.

In a particular embodiment, as shown in FIG. 9C, actuator 600 may include a body 602 having a finger-contacting portion 604 that is angled with respect to a lower projection 608 extending from the body 602. A flange 606 may also extend from body 602 (e.g., similar in construction to flange 306), and a bore 610 may be formed through body 602. However, different from actuator 300, lower projection 608 of actuator 600 may include a lever 650.

In use, fixing member 562 may be engaged with plates 21, 22 in much the same manner as fixing member 262, except that, once teeth 578 of fixing member 562 are engaged with teeth 30 on plates 21, 22, lower projection 608 of actuator 600 may be offset from wall 630 of fixing member 562 via interaction between lever 650 and a portion of pivotal bar 61. This is shown in detail in FIG. 9D in which lever 650 is resting upon pivotal bar 61 causing lower projection 608 to be offset from wall 630. From this orientation, a user may therefore actuate actuator 600 (e.g., using his or her thumb, as previously described) in much the same manner as actuator 300 to move post 80 in the direction indicated by arrow 640 in FIG. 9D. In short, through actuation of actuator 600, flange 606 may press upon a surface of pin 75 causing fixing member 562 to lift off teeth 30 on plates 21, 22 and move in the direction of arrow 640. Such is discussed in more detail above in connection with actuator 300 of FIGS. 7A-D, and it is contemplated that actuator 600 may operate in the same manner.

Figure 9E:
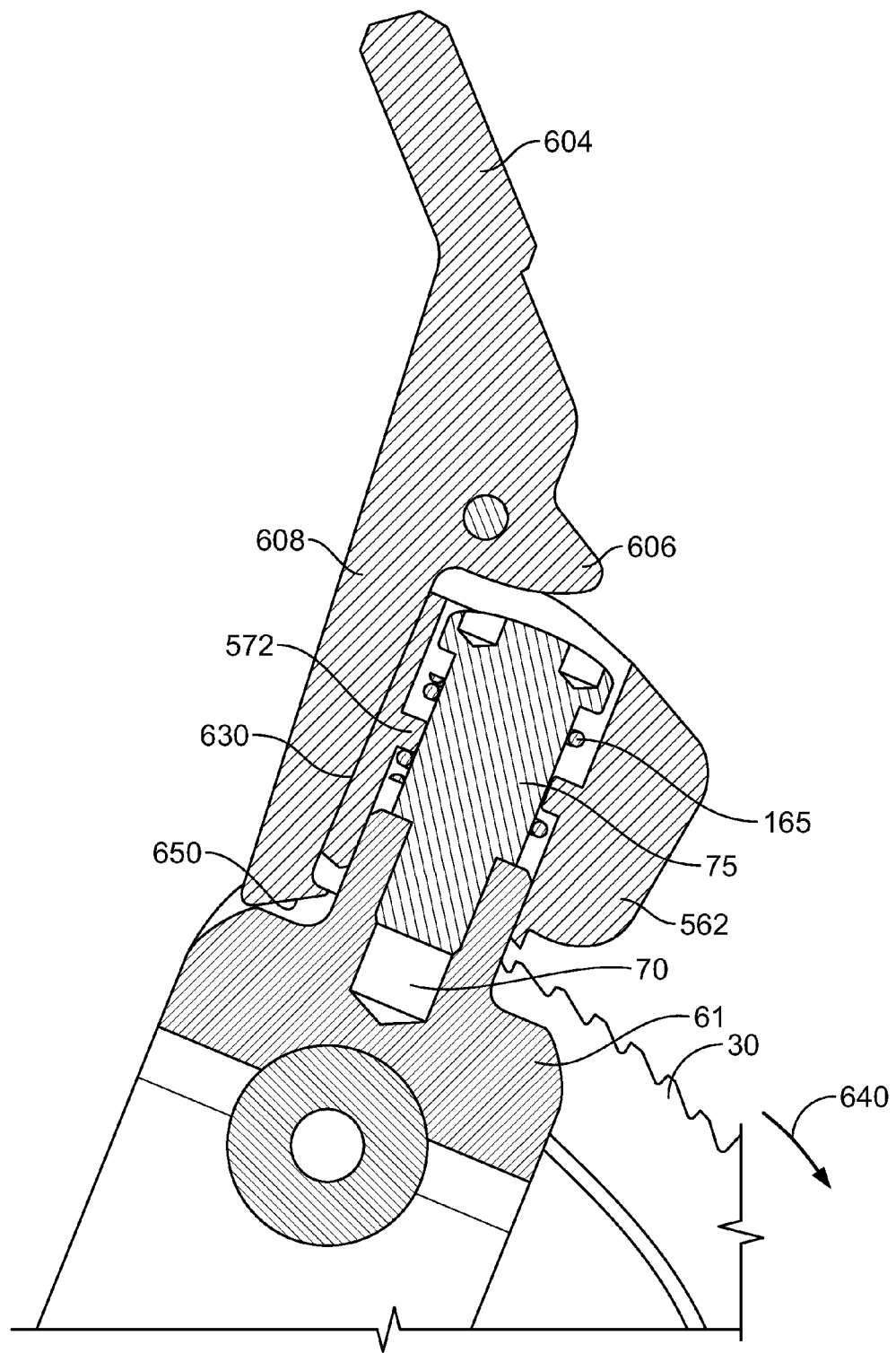

It is also contemplated, however, that with the inclusion of lever 650, actuator 600 may perform a like function in a direction opposite arrow 640. In other words, upon pressing actuator 600 in a direction away from arrow 640, a surface of lever 650 may engage with a portion pivotal bar 61 to lift teeth 578 of fixing member 562 off of teeth 30 on plates 21, 22. This may allow easier translation of post 80 and fixing member 562 in a direction opposite arrow 640. Such lifting function is shown in detail in FIG. 9E, and allows a user to move post 80 in a direction away from arrow 640 with teeth 578 on fixing member 562 disengaged from teeth 30 on plates 21, 22. Once released (e.g., after post 80 has been moved), actuator 600 may assume its normal position. In other words, lever 650 may re-assume its resting position on pivotal bar 61, and teeth 578 on fixing member 562 may re-engage with teeth 30 on plates 21, 22 to fix fixing member 562 in place. Thus, adjustment mechanism 560 permits a user to move post 80 and fixing member 562 either in the direction of arrow 640 (e.g., as discussed in detail in connection with FIGS. 7A-D), or in an opposite direction, via lifting of fixing member 562 off of teeth 30 on plates 21, 22 by way of actuator 600.

Figure 10A:
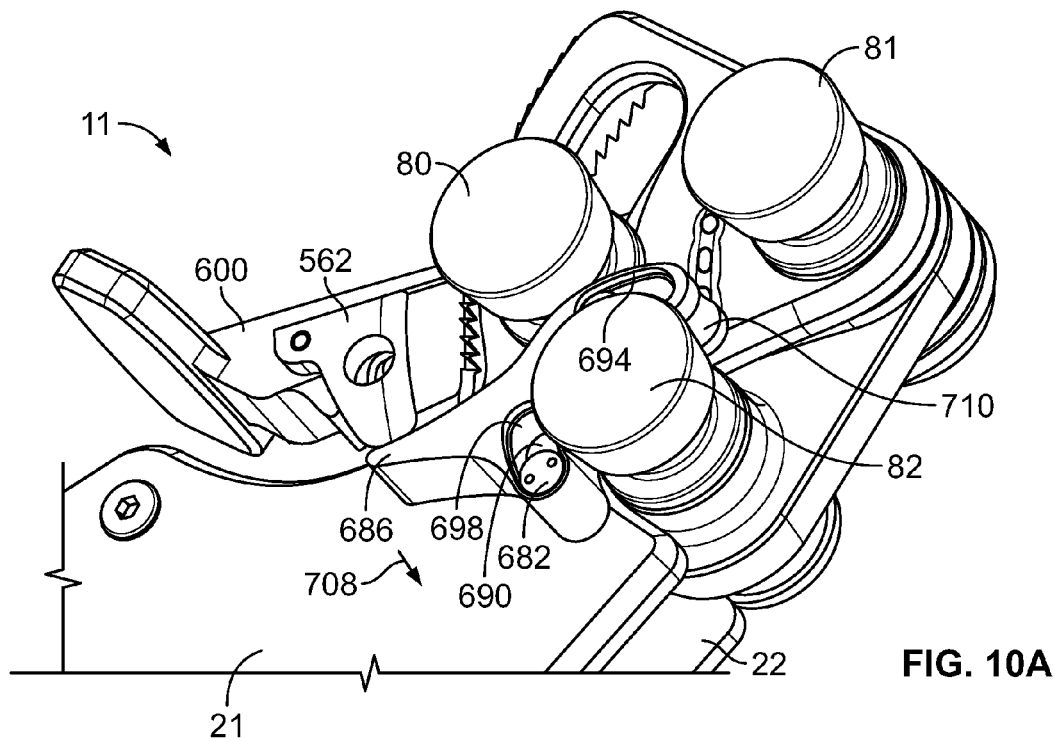
FIGS. 10A-B are perspective and side views, respectively, of a retaining mechanism utilized with an instrument for bending surgical devices, according to another embodiment of the invention.
Figure 10B:
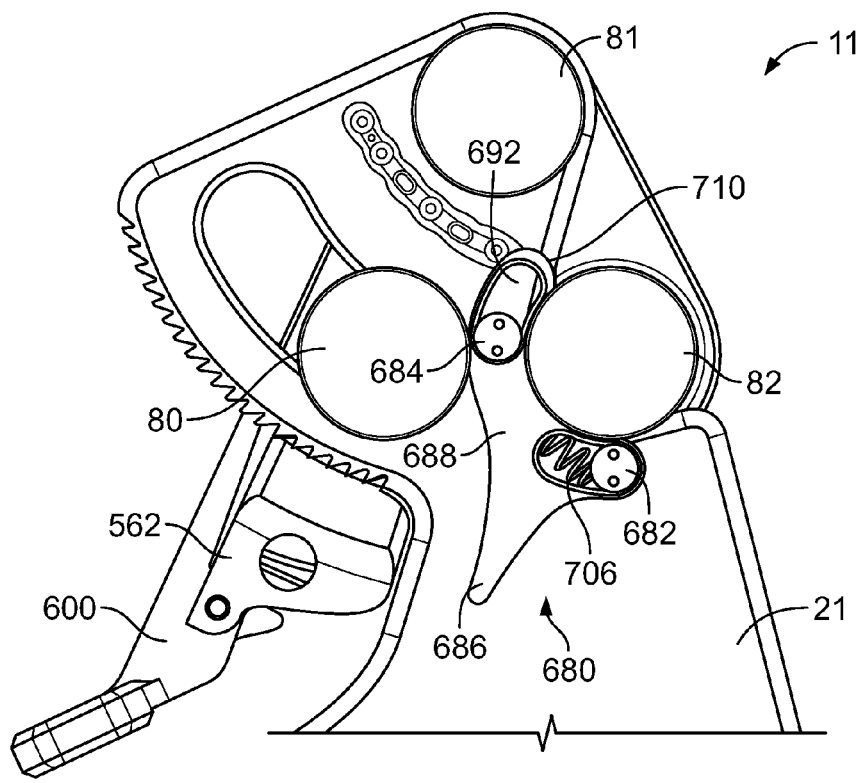

A retaining mechanism 680 may also be included with bender 11, in certain embodiments, as shown in FIGS. 10A-B. Retaining mechanism 680 may be used to temporarily restrain or stabilize surgical device 180 with respect to bender 11 prior to bending thereof. In a particular embodiment, retaining mechanism 680 may include a body 688 having a set of elongate apertures 690, 692 and an actuator 686 extending from the body 688. Apertures 690, 692 may include a first recessed section 694 having a lip extending around a perimeter of section 694, and a second section 698 that is narrower than first section 694. A set of pegs 682, 684 may also be provided for engaging retaining mechanism 680 to plate 21 through apertures 690, 692. Indeed, first recessed section 694 of apertures 690, 692 may be configured to receive a head of pegs 682, 684, while second section 698 may be configured to receive a shaft of pegs 682, 684. Further, pegs 682, 684 may be screwed into plate 21 to secure retaining mechanism 680 to plate 21. In one embodiment, aperture 690 also includes a spring 706 or other compressible member situated therein for engaging with peg 682 during movement of retaining mechanism 680 (FIG. 10B). Spring 706 is omitted for convenience in FIG. 10A so that the interior of aperture 690 is viewable.

The operation of retaining mechanism 680 may be as follows. With retaining mechanism 680 attached to plate 21 (e.g., via the insertion of pegs 682, 684 through mechanism 680 and into plate 21), a user may situate surgical device 180 amongst posts 80, 81, 82. Surgical device 180 may be situated amongst posts 80, 81, 82, for example, according to the image of surgical device 180 on bender 11 (FIGS. 10A-B). Prior to and/or during positioning of surgical device 180 about posts 80, 81, 82, the user may also utilize his/her finger(s) to depress actuator 686 in the direction of arrow 708 in FIG. 10A, thereby causing body 688 to move and pegs 682, 684 to translate within apertures 690, 692. Then, with surgical device 180 between posts 80, 81, 82, the user may release actuator 686 so that a surface 710 of retaining mechanism 680 contacts surgical device 180 and forces surgical device 180 against at least post 81 (and potentially each or more than one of posts 80, 81, 82). The forces borne on surgical device 180 by surface 710 of retaining mechanism 680 may be a result of compression of spring 682 during initial movement of mechanism 680, of course.

In this manner, surgical device 180 may be temporarily restrained within bender 11 by at least surface 710 of retaining mechanism 680. The user may then utilize adjustment mechanism 560, or any of the previously-described adjustment mechanisms (if retaining mechanism 680 is included in those embodiments), to move post 80 against surgical device 180 and lock surgical device 180 in place. Then, bending of device 180 may occur via movement of post 82 and actuation of lever 40. Indeed, bending of surgical device 180 may occur substantially as described previously once surgical device 180 is situated amongst posts 80, 81, 82 and retained in place by way of retaining mechanism 680. Retaining mechanism 680 may therefore provide a secure way to hold and/or stabilize surgical device 180 with respect to bender 11 prior to bending device 180 and/or moving post 80 to lock device 180 in place.

Figure 8A:
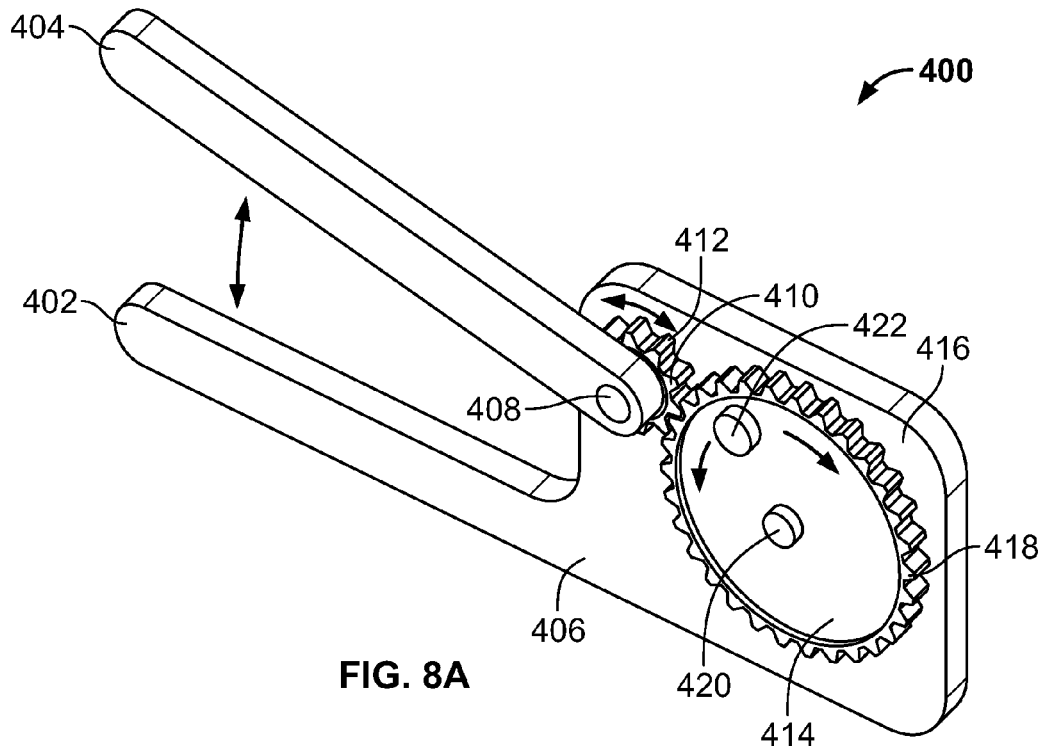
FIGS. 8A-B are top and bottom perspective views, respectively, of an alternate apparatus for bending surgical devices, according to another embodiment of the present invention.
Figure 8B:
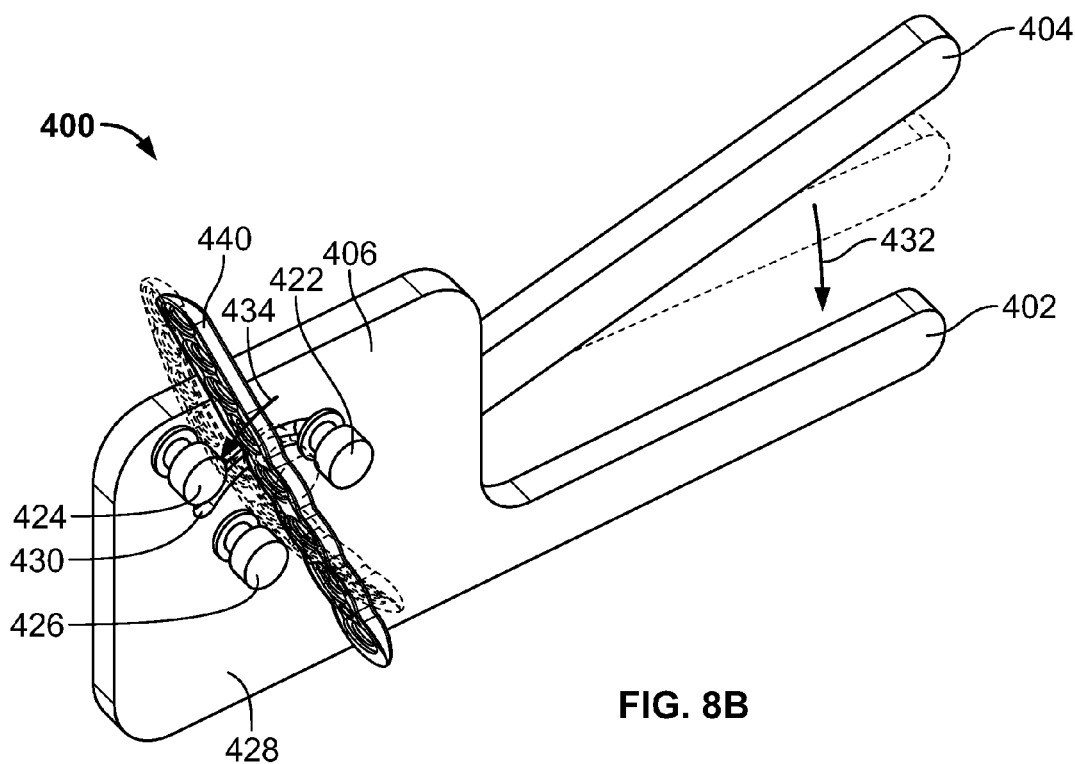

An alternate tool 400 for bending a surgical device, according to another embodiment of the present invention, is shown in detail in FIGS. 8A-B. Here, tool 400 may function to bend a surgical device according to the contour of the bone being operated on, as with tool 10, but tool 400 is configured to operate differently. In particular, tool 400 may include first and second handles 402, 404, one handle 402 being stationary, in one embodiment, and the other 404 being movable. Indeed, handle 404 may be movable about a connection point with a body 406 of tool 400, such connection point being established via the insertion of a pin 408 through respective bores (not shown) formed in both handle 404 and body 406 of tool 400. Thus, handle 404 may be rotatable or movable about pin 408, as exemplified by arrow 432 in FIG. 8B and the dotted lines showing the change in position of handle 404.

Referring to FIG. 8A, handle 404 may also have, connected at one end thereof, a wheel 410 including serrations or gears 412. Thus, upon movement of handle 404 about pin 408, wheel 410 (and gears 412) may move or rotate about pin 408. FIG. 8A also depicts a second wheel 414 situated on a bottom surface 416 of body 406, such wheel 414 including teeth or gears 418 as well. In one embodiment, a pin 420 may connect wheel 414 to body 406 to thereby allow wheel 414 to rotate freely. What is more, in some instances, wheel 410 of handle 404 may engage with wheel 414 on body 406 so as to cause rotation of wheel 414 once handle 404 is actuated.

FIGS. 8A-B, in combination, also depict a set of posts 422, 424, 426 connected to a top surface 428 of body 406 of tool 400, two (2) of such posts 424, 426 being stationary on top surface 428, and one (1) of such posts 422 being movable within a slot 430 formed in body 406. In a particular embodiment, movable post 422 may be connected to a portion of wheel 414, such that rotation of wheel 414 may cause movement of post 422 within slot 430. As wheel 414 may be circular in one embodiment, such movement of post 422 may be generally circumferential, and slot 430 may be curved to accommodate the circumferential movement of post 422, although other configurations of slot 430 are contemplated.

In use, one may first situate a surgical device 440, shown in FIG. 8B as a bone plate, amongst posts 422, 424, 426. Then, the user may grasp handles 402, 404 and squeeze handle 404 towards handle 402 in the direction of arrow 432, thus causing wheel 410 to engage with wheel 414. Upon movement or squeezing of handles 402, 404, as described, wheel 410 may cause wheel 414 to rotate via the interaction between gears 412, 418, ultimately resulting in movement of post 422 within slot 430. This movement of post 422 may be generally within slot 430 and between posts 424, 426 so as to bend the surgical device 440. In particular, post 422 may force surgical device 440 against posts 424, 426 causing such device 440 to bend according to the amount of travel of post 422. Such movement is exemplified by the arrow 434 adjacent post 422, as well as the dotted lines depicting both the movement of post 422 and the corresponding bending of surgical device 440. Thus, the user may squeeze handles 402, 404 a particular amount to cause surgical device 440 to bend more or less according to the length of travel of handle 404 (and thus wheel 414 and post 422).

In some embodiments, there may be particular indicia or a scale (not shown) on body 406 of tool 400 allowing the user to determine the particular amount that the surgical device 440 has been bent. Once bending is complete, handles 402, 404 may simply be released and surgical device 440 removed from posts 422, 424, 426. This bending procedure may also be repeated, if necessary, for further bending of surgical device 440.

In the devices depicted in the figures, particular structures are shown that are adapted to provide improved apparatus for bending surgical devices. The invention also contemplates the use of any alternative structures for such purposes, including structures having different lengths, shapes, and/or configurations. For example, while wrench 110 is depicted in the figures as a manual tool, it is equally contemplated that wrench 110 may be connected to a power source to operate as a power tool. Thus, rather than rotate wrench 110 manually, a user may utilize a powered wrench 110 to rotate pinion 140 against rack 41. This same modification may apply to the alternate tool 400 shown in FIGS. 8A-B. In particular, as opposed to using a manually-operated handle 404, it is contemplated that a powered device 400 may be provided, and that the interaction between wheels 410, 414 may be power operated instead of manual. For instance, a small electric motor may be provided with tool 400 to cause movement of wheels 410, 414 and thus post 422. It is also contemplated that wrench 110 may be utilized with tool 400. In short, structure may be provided on tool 400 allowing engagement of wrench 110 with gears 418 on wheel 414.

Further, while in the main embodiment handle 120 and pinion 140 of wrench 110 are rotatable in conjunction with one another, ratchet-type structure may be included with wrench 110, as previously described. In this and other embodiments, it is also contemplated that a pawl (not shown) may be included adjacent pinion 140 for selectively allowing pinion 140 to move in only one direction. Thus, with the inclusion of a pawl (not shown) into, for example, a portion of the housing 20 of bender 11, a user may rotate handle 120 of wrench 110 causing rotation of pinion 140, and such pinion 140 may be locked or selectively prevented from rotating in the reverse direction. As such, upon bending surgical device 180 some particular amount, and upon release of handle 120 by a user, surgical device may be retained within posts 80, 81, since such posts would not change orientation. In one embodiment, with the addition of ratchet-type structure noted above, the user may simply rotate handle 120 from its rotated position back to its initial position with pawl (not shown) retaining pinion 140 (and thus posts 80, 81, 82) in place. Then, the user may re-rotate handle 120 to continue to bend surgical device 180, as desired. To finally release the tension built up between pinion 140 and rack 41 via pawl, one may simply release the pawl from engagement within pinion 140 and allow posts 80, 81, 82 to assume their natural unstressed condition. Alternatively, it is also contemplated that pawl may be situated to engage with rack 41 instead of pinion 140 to achieve the same effect as described above. With the addition of a pawl, it may also be easier for a user to read angular indicia 42 on lever 40, as wrench 110 may be entirely removed from connection with bender 11 without posts 80, 81, 82 changing orientation with respect to one another.

As another example, although post 80 is described as being movable within elongate slot 28 in plates 21, 22, post 80 may alternatively be fixed within plates 21, (e.g., via an aperture similar to aperture 27). Further, additional posts beyond posts 80, 81, 82 may be included in bender 11, whether circumferentially movable as with post 82, movable within a slot as with post 80, or fixed as with post 81. Thus, more posts beyond the three (3) posts 80, 81, 82 shown may be included with bender 11. The same is true of posts 422, 424, 426 of tool 400 (e.g., more posts beyond those shown may be included with tool 400). In some embodiments, these additional posts may provide further points of stabilization for surgical devices 180, 440 once situated amongst the posts.

In addition, while slot 430 formed in body 406 of tool 400 is curved in one embodiment, slot 430 may also be rectangular, or any other shape, provided slot 430 allows post 422 to move adequately and bend surgical device 440 during use of tool 400. The same is true of slot 28 formed in plates 21, 22.

It is also contemplated that, while movement of fixing members 62, 262 is described as being more difficult in one direction, and easier in an opposing direction, these directions may be reversed. In other words, it is contemplated that the angle of teeth 78, 278 on fixing members 62, 262 and teeth 30 on plates 21, 22 may be angled differently to accommodate different movement of post 80 (and thus fixing members 62, 262).

Although surgical device 180 is shown as being oriented in one fashion in FIGS. 6A-B for bending, it is also contemplated that surgical device 180 may be oriented in other ways amongst posts 80, 81, 82 (e.g., as reflected by the image of surgical device 180 on bender 11 in FIGS. 10A-B). In short, surgical device 180 may be situated in various ways amongst posts 80, 81, 82 so long as effective bending may occur.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will also be appreciated that the various dependent claims and the features set forth therein can be combined in different ways than presented in the initial claims. It will also be appreciated that the features described in connection with individual embodiments may be shared with others of the described embodiments.

The invention claimed is:

1. A system for bending a surgical device comprising:
a surgical device implantable into a body of a patient; and
a bending apparatus including a housing with at least a first and a second post, the first and second posts being fixable in location during bending;
a third circumferentially movable post engaged with the housing;
a first actuator having a first multi-toothed gear mechanism;
a second multi-toothed gear mechanism configured to intermesh with the first multi-toothed gear mechanism so that, upon intermeshing the first and second multi-toothed gear mechanisms, the third post is movable circumferentially via rotation of the multi-toothed gear mechanisms and the surgical device is bendable about at least one of the first and second posts;
an adjustment mechanism having a body, at least a portion of which includes serrations; and
a second actuator,
wherein at least one of the first and second posts resides within an elongate slot in the housing, and the at least one of the first and second posts is movable within the slot in a first orientation, and fixed within the slot in a second orientation,
wherein at least a portion of the housing adjacent the elongate slot includes serrations for engaging with the serrations on the body of the adjustment mechanism, and
wherein the second actuator is adapted to be actuated such that when the at least one of the first and second posts is in the first orientation, all of the serrations on the body of the adjustment mechanism are separated from all of the serrations adjacent the elongate slot of the housing to allow the at least one of the first and second posts to move within the elongate slot.

2. The system of claim 1, wherein the third post is configured to move circumferentially upon rotation of the first actuator about a longitudinal axis thereof.

3. The system of claim 1, wherein the second actuator includes a surface adapted to contact a pivotal member engaged with the at least one of the first and second posts.

4. The system of claim 1, wherein movement of the at least one of the first and second posts within the elongate slot is easier in one direction, and more difficult in another opposing direction.

5. The system of claim 1, wherein the first actuator comprises a shaft having a longitudinal axis, and the shaft is configured to cause circumferential movement of the third post upon rotation of the shaft about the shaft's longitudinal axis.

6. The system of claim 5, wherein:
a distal end of the shaft includes a pinion and the third post is engaged with a lever having a rack,
and wherein the pinion is connectable with the rack and is configured to move the rack upon rotation of the shaft about its longitudinal axis.

7. The system of claim 1, wherein a portion of the bending apparatus includes angular indicia thereon for determining the degree to which the surgical device is bent.

8. The system of claim 1, wherein the first and second multi-toothed gear mechanisms are manually-operable gear mechanisms.

9. The system of claim 1, wherein the first multi-toothed gear mechanism of the first actuator is selectively engageable and removable from the second multi-toothed gear mechanism.

10. The system of claim 1, further comprising a retaining mechanism engaged with the bending apparatus, the retaining mechanism being movable via a retaining mechanism actuator from a first position to a second position, and being biased to remain in the first position.

11. The system of claim 10, wherein a surface of the retaining mechanism, once moved to the second position, is adapted to engage the surgical device and force the device against at least one of the first, second, and third posts.

12. The system of claim 10, wherein the retaining mechanism is biased to remain in the first position via a spring engaged with the retaining mechanism.

13. A method of bending a surgical device comprising:
providing a bending apparatus having a housing with at least first, second, and third posts, the third post being circumferentially movable;
moving at least one of the first and second posts within an elongate slot in the housing by manipulating a second actuator of an adjustment mechanism to separate the adjustment mechanism from the housing to permit the at least one of the first and second posts to move within the elongate slot;
providing a first actuator that is movable between a first position and a second position to move the third post circumferentially, a first multi-toothed gear mechanism of the first actuator being engageable with a second multi-toothed gear mechanism of a structure attached to the third post;
positioning a surgical device amongst the first, second, and third posts; and
engaging and rotating the first multi-toothed gear mechanism of the first actuator against the second multi-toothed gear mechanism of the structure to move the third post circumferentially and bend the surgical device about at least one of the first and second posts.

14. The method of claim 13, further comprising the step of fixing the at least one of the first and second posts within the elongate slot after the at least one of the first and second posts has been moved.

15. The method of claim 13, wherein the adjustment mechanism includes a body having serrations, and at least a portion of the housing includes serrations adapted to engage with the serrations on the body of the adjustment mechanism,
and wherein actuation of the second actuator causes the serrations on the body of the adjustment mechanism to disengage from the serrations on the housing to permit movement of the at least one of the first and second posts within the elongate slot.

16. The method of claim 13, wherein the bending apparatus includes a lever having a rack, and the method further comprises the step of contacting the rack with a pinion formed on the first actuator to move the third post circumferentially.

17. The method of claim 13, further comprising the step of stabilizing the first actuator with respect to the housing by inserting a shaft of the actuator through an aperture in a first plate of the housing and into a corresponding aperture in a second plate of the housing.

18. The method of claim 13, further comprising manually rotating the first actuator and the first multi-toothed gear mechanism against the second multi-toothed gear mechanism so as to cause the third post to move circumferentially.

19. A system for bending a surgical device comprising,
a surgical device implantable into a body of a patient; and
a bending apparatus for bending the surgical device comprising:

a housing including first, second, and third posts, at least the third post being circumferentially movable about the housing;

a first actuator having a first multi-toothed gear mechanism that is movable between a first position and a second position; and a second multi-toothed gear mechanism adapted to engage with the first multi-toothed gear mechanism, the second multi-toothed gear mechanism being movable upon movement of the first actuator between the first position and the second position, wherein movement of the second multi-toothed gear mechanism causes movement of the third post circumferentially so as to bend the surgical device about at least one of the first and second posts;

an adjustment mechanism having a body, at least a portion of which includes serrations; and a second actuator, wherein the first post is movable within an elongate slot in the housing in a first orientation and fixed within the slot in a second orientation, wherein at least a portion of the housing adjacent the elongate slot includes serrations for engaging with the serrations on the body of the adjustment mechanism, and wherein the second actuator is adapted to be actuated such that when the first post is in the first orientation, all of the serrations on the body of the adjustment mechanism are separated from all of the serrations adjacent the elongate slot of the housing to allow the first post to move within the elongate slot.

20. The bending apparatus of claim 19, wherein the first actuator comprises a shaft with an end having a pinion, the pinion comprising the first multi-toothed gear mechanism.

21. The bending apparatus of claim 19, wherein the third post is attached to a lever rotatable about the second post, the second post being inserted through the lever and the housing and engaging the lever and the housing together.

* * * * *